(12) United States Patent
Miller et al.

(10) Patent No.: US 7,490,049 B2
(45) Date of Patent: Feb. 10, 2009

(54) PATIENT ORIENTED POINT OF CARE SYSTEM AND METHOD

(75) Inventors: Ian Michael Miller, Summit, NJ (US); Mark J. Halloran, Long Valley, NJ (US); Lynn A. Petersen, Oakland, NJ (US); Donna T. Whiteford, Brooklyn, NY (US); Dorian King-Cheung Lo, Bloomingdale, NJ (US); Patrice Bavaro, Morristown, NJ (US); Anthony J. Schueth, Morristown, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 1063 days.

(21) Appl. No.: 10/109,042

(22) Filed: Mar. 29, 2002

(65) Prior Publication Data

US 2003/0187690 A1    Oct. 2, 2003

(51) Int. Cl.
    *G06Q 50/00*    (2006.01)
(52) U.S. Cl. .................. 705/3; 705/2; 701/32; 128/903; 128/920; 177/25.19; 604/20; 604/131
(58) Field of Classification Search ...................... 705/2, 705/3; 701/32; 128/903, 920; 177/25.19; 604/20, 131
    See application file for complete search history.

(56) References Cited

U.S. PATENT DOCUMENTS

| 5,471,382 | A | 11/1995 | Tallman et al. |
| 5,544,044 | A | 8/1996 | Leatherman |
| 5,550,734 | A | 8/1996 | Tarter et al. |
| 5,619,991 | A | 4/1997 | Sloane |
| 5,666,492 | A | 9/1997 | Rhodes et al. |

(Continued)

FOREIGN PATENT DOCUMENTS

CA    2027000    4/1992

(Continued)

OTHER PUBLICATIONS

Rx Scan, Muirhead, Greg; Drug Topics; Oradell; Nov. 7, 1994.*

*Primary Examiner*—C Luke Gilligan
*Assistant Examiner*—R. David Rines
(74) *Attorney, Agent, or Firm*—Irah H. Donner; Wilmer Cutler Pickering Hale and Dorr LLP

(57) ABSTRACT

Computer-assisted methods, systems and mediums for providing, to a physician, information relating to a patient. One embodiment of the present invention is a method that comprises the steps of collecting a prescription history that includes information relating to one or more prescriptions issued to the patient and a prescription purchase history, storing the prescription history and prescription purchase history of the patient into a database, and accessing, by the patient, the database for the stored prescription history and prescription purchase history of the patient. The prescription purchase history includes information relating to one or more prescription purchases made by the patient in accordance with the one or more prescriptions. The method also includes the steps of retrieving the prescription history and prescription purchase history by the patient, and communicating, by the patient, the retrieved prescription history and prescription purchase history to the physician via physically or electronically in order to assist the physician in providing medical services to the patient.

48 Claims, 21 Drawing Sheets

U.S. PATENT DOCUMENTS

| | | | |
|---|---|---|---|
| 5,704,044 A | 12/1997 | Tarter et al. | |
| 5,713,485 A | 2/1998 | Liff et al. | |
| 5,737,396 A | 4/1998 | Garcia | |
| 5,737,539 A | 4/1998 | Edelson et al. | |
| 5,740,428 A | 4/1998 | Mortimore et al. | |
| 5,758,095 A | 5/1998 | Albaum et al. | |
| 5,781,442 A | 7/1998 | Engleson et al. | |
| 5,797,515 A | 8/1998 | Liff et al. | |
| 5,845,254 A | 12/1998 | Lockwood et al. | |
| 5,845,255 A * | 12/1998 | Mayaud | 705/3 |
| 5,910,107 A | 6/1999 | Iliff | |
| 5,923,018 A | 7/1999 | Kameda et al. | |
| 5,924,074 A | 7/1999 | Evans | |
| 5,950,207 A | 9/1999 | Mortimore et al. | |
| 5,950,630 A | 9/1999 | Portwood et al. | |
| 5,964,700 A | 10/1999 | Tallman et al. | |
| 5,970,462 A | 10/1999 | Reichert | |
| 5,994,110 A | 11/1999 | Mosbach et al. | |
| 6,022,315 A | 2/2000 | Iliff | |
| 6,066,243 A | 5/2000 | Anderson et al. | |
| 6,067,523 A | 5/2000 | Bair et al. | |
| 6,068,156 A | 5/2000 | Liff et al. | |
| 6,082,776 A | 7/2000 | Feinberg | |
| 6,421,650 B1 * | 7/2002 | Goetz et al. | 705/3 |
| 6,988,075 B1 * | 1/2006 | Hacker | 705/3 |

FOREIGN PATENT DOCUMENTS

| | | |
|---|---|---|
| CA | 2201311 | 5/1996 |
| EP | 0800680 | 8/1998 |
| JP | 64-051574 | 2/1989 |
| JP | 05-143620 | 6/1993 |
| JP | 07-311807 | 11/1995 |
| JP | 08-018020 | 1/1996 |
| JP | 09-094287 | 4/1997 |
| JP | 09-245095 | 9/1997 |
| JP | 10/250157 | 9/1998 |
| WO | WO 96/13790 | 5/1996 |
| WO | WO 99/39298 | 8/1999 |
| WO | WO 99/44167 | 9/1999 |
| WO | WO 99/45490 | 9/1999 |
| WO | WO 00/41613 | 7/2000 |

* cited by examiner

408

| Welcome, John | VIEW MESSAGE CENTER |

Managing your prescriptions

> There are 2 mail service prescriptions ready for refill:
> -Metoprolol Tartrate Tabs, prescribed for Gina
> -Carisoprodol Tabs, prescribed for John
> Visit My Prescriptions to refill now!

407

| Managing your health | view more |

Medication Know-How

> Have you had trouble remembering to take your arthritis medications? Here are some tips that may help.

> Medications should be taken as prescribed by your doctor or other healthcare professional. Learn more about why you should be taking your cholesterol medication as prescribed.

Know Your Risks

> About one in every four adults has high blood pressure, a risk factor for kidney failure, heart attack and stroke. Learn about hypertension and speak to your health care professional.

> Are your cholesterol levels putting your heart health at risk? Find out.

Practical Tip

> If you've had a heart attack, lower your cholesterol and you may reduce your chance of having another one.

Site features

> New Feature - My Doctor Visit!
> Just click here for easy access to personalized tools you can use to help you and your doctor make more informed decisions about the medications you need to stay healthy.

> Need to know your prescription coverage and pricing information?
> Find out by visiting our prescription coverage and pricing feature today! Here you'll find out what you will pay for both brand-name and generic medications based on your plan's coverage guidelines.

| PRESCRIPTION COVERAGE & PRICING | REFILL HOUSEHOLD PRESCRIPTIONS | HOUSEHOLD RX STATUS | (?) |

<u>503</u>  <u>505</u>  <u>507</u>

| Mail Prescriptions | Retail Prescriptions | Rx Archive |

My Doctor Visit
Items in cart: 0

View orders by: [Refillable/Renewable ▼] 🗋          Print this page

You have 2 prescription(s) in your Rx Archive. <u>Click here to view.</u>

Click on the Prescription Number(s) below for the detailed history for this prescription.
Click on the Drug Name(s) below for the detailed history about this medication.  ⟵305

| | Prescription (Rx) Number<br>Drug information<br>Patient Name | Date<br>Received | Date<br>Shipped | Refills<br>Remaining |
|---|---|---|---|---|
| 🛒<br>ADD TO<br>CART | <u>123456789012</u> ✉<br><u>Metoprolol Tartrate Tabs</u>   50mg<br>Gina<br><br>Status: Ready for refill.<br>This prescription can be refilled today! To order this prescription, simply select the "add to cart" option in the first column of this row. | Oct 2, 2000 | Oct 6, 2000 | 3<br>after this refill |
| 🛒<br>ADD TO<br>CART | <u>992310090501</u> ✉<br><u>Carisoprodol tabs</u>   350mg<br>John<br><br>Status: Shipped Oct 20, 2001.<br>This prescription was shipped via United States Postal Service.<br>To remove this prescription from view, click here to add to Rx Archive. | Oct 15, 2000 | Oct 20, 2000 | 2<br>after this refill |
| | <u>992310090501</u> ✉<br><u>Nasonex Nasal Spray</u>   50mcg<br>Gina<br><br>Status: Shipped Dec 29, 2001.<br>This prescription was shipped via United States Postal Service.<br>To remove this prescription from view, click here to add to Rx Archive. | Dec 28, 2000 | Dec 29, 2000 | 2<br>after this refill |
| 🛒<br>ADD TO<br>CART | <u>992310091501</u> ✉<br><u>K-dur sr tabs</u>   20meq<br>John<br><br>Status: Prescription Pended.<br>This prescription was requested prior to the eligible refill date. For your convenience, your mail service pharmacy is holding this prescription and will process this prescription on Feb 03, 2001. Please check order status after this date.<br>To remove this prescription from view, click here to add to Rx Archive. | Dec 28, 2000 | | 1<br>after this refill |

FIG. 5

SEARCH [        ] (Go)

Gina's Health

Health Centers
- Arthritis Center
- Cardiovascular Center
- Digestive Health Center
- Respiratory Center
- Wellness and Prevention Center
- Women's Health Center

Health Topics
- Allergies
- Asthma
- Diabetes
- Diet and Nutrition
- Disease Awareness
- Exercise
- Health and Wellness
- Healthy Aging
- Heart Health
- Hepatitis and Liver Disease
- Medication and Prescription Drug Use
- Men's Health
- Mental Health
- Multiple Sclerosis
- Smoking Cessation
- Women's Health

Tools
- Health Profile Calculator
- Rate Your Pain
- more tools...

Resources
- Ask the Pharmacist
- Audio Health News
- Health Organizations
- Health References
- My Doctor Visit
- Product Alerts welcome to My Health

My Centers        612        (edit)

Go to your selected Health Centers:
Wellness and Prevention Center

My Interests            (edit)

NOTE: The Diet & Nutrition, Exercise, Health & Wellness and Medication and Prescription Drug Use health interest categories will no longer appear in this area. They have been rolled into the new Wellness & Prevention Health Center. If you have previously chosen any of these categories, your profile will automatically reflect this change. See our new Health Interest offerings and update your profile by clicking the edit button.

Exercise

LATEST NEWS
> Too Much Exercise Can Make You Sick
  High volume training requires adequate amounts of rest
> Celebrate Your 40th By Taking Up Weight Training
  The older you get, the more you need it

Diet & Nutrition

LATEST NEWS
> Don't Like Healthful Foods? Try Tricking Yourself
  Add foods good for you to your diet, but do it slowly.
> Moo-ther Knows Best
  Want healthy daughters? Drink milk, not soda.

605 → (Health Centers)
607 → (Health Topics)
609
611
306

FIG. 6

Find a Product:    My Store

 MY SHOPPING LIST

| Health and Wellness Products | Household Needs | Personal Care |
|---|---|---|
| Allergy, Sinus & Asthma | Arts & Crafts | Baby |
| Baby | Audio, Video & CDR | Bath Boutique |
| Cough & Cold | Cameras & Film | Deodorants |
| Diabetes Care | Flashlights & Batteries | Ear & Eye Care |
| Diet & Nutrition | Household Storage | Family Planning |
| Ear & Eye Care | Lighting | Feminine Hygiene |
| More... | More... | More... |
| Online Specials... | Online Specials... | Online Specials... |
| Photo Store | Vitamins and More | |
| Cameras & Film | Aromatherapy | |
| Flashlights & Batteries | Diet & Nutrition | |
| More... | Flower Essences | |
| Online Specials... | Herbs & Herbal Teas | |
| | Homeopathic | |
| | Minerals | |
| | More... | |
| | Online Specials... | |

CVS Super Savers

  CVS Ibuprofen Tablets Coated CVS
Ibuprofen Tablets Coated
*500 Tablets*
details
~~$12.19~~ $6.99
 ADD TO CART

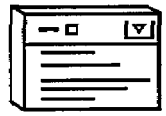 CVS Cimetidine Tablets 200 Mg
CVS Cimetidine...acid
*50 Tablets*
details
~~$10.99~~ $4.99
 ADD TO CART

308

FIG. 8

| My Doctor Visit |  |

| What's Included |
|---|
| Medication history |
| Patient requests |
| Benefit information |
| Formulary quick guide |
| Prescription fax form |

905

Patient name: | John- D.O.B. 07/29/1969 ▼ | 903

My Doctor Visit

Now that you have selected a patient name, you may view any of the individual My Doctor Visit elements by selecting from the menu that appears to the left.

You may also elect to print the entire My Doctor Visit kit by clicking the "Print The Kit" button that appears above.

You can grant access to your covered spouse/domestic partner to view and manage your household's prescription history by updating your merckmedco.com online profile. To update your online profile to permit Household view, simply click on the "My Profile" option on the bottom menu bar of this page and select the "Update personal online preferences" option. Then, scroll down to the bottom of this page and select "yes" in the Household View section. Be certain to submit your changes so that we receive them and update your profile accordingly.

COPYRIGHT AND LEGAL INFORMATION
USE OF INFORMATION

FIG. 9

| My Doctor Visit | | | | | Print The Kit | (?) |

> My Doctor Visit

| What's Included |
|---|
| Medication history |
| Patient requests |
| Benefit information |
| Formulary quick guide |
| Prescription fax form |

Patient name: | John- D.O.B. 07/29/1969 | ▼ |

Medication history

This section of My Doctor Visit lists all available prescription information for the patient selected above.

Sharing this information with your doctor is important, especially if you are seeing more than one physician. It can help ensure that your doctor is aware of every medication your plan is providing. Your doctor can use this information to avoid possible drug interactions when prescribing drugs for you.

✉  prescription filled through your mail-service pharmacy
👤  prescription filled at a retail (walk-in) pharmacy

| Prescription (Rx) number/ Medication name/ strength | Rx filled at | Date filled | Qty | Days supply | Days past refill date |
|---|---|---|---|---|---|
| #123456789012 Cholestyramine 250mg | 👤 | 11/31/00 | 60 | 30 | 30 |
| #123456789013 Cholestyramine 250mg | 👤 | 10/31/00 | 60 | 30 | 60 |
| #123456789014 Lotensin 100mg | ✉ | 11/04/00 | 180 | 90 | 0 |
| #123456789015 Lotensin 100mg | ✉ | 08/04/00 | 180 | 90 | 30 |

1003 → (points to first row)

FIG. 10

| My Doctor Visit | Print The Kit |  |

> My Doctor Visit

| What's Included |
| --- |
| Medication history |
| Patient requests |
| Benefit information |
| Formulary quick guide |
| Prescription fax form |

Patient name: | John- D.O.B. 07/29/1969 | ▼ |

Patient requests

This area lists for your doctor, any prescription related requests you have made over the last seven days including requests to switch your retail prescriptions to our convenient mail service pharmacy.

Note: These requests may reflect multiple prescribing doctors

---

*John* has made the following request(s):

☐ Renewal for <<drug name>> a medication he/she is currently taking prescribed by <<doctor name>>.

Action: If you have not already done so, please respond to the renewal request received from Merck-Medco on *John's* behalf.

Pharmacy change for <<drug name>> prescribed by <<doctor name>> to our mail service pharmacy.

Action: If you have not already done so, please respond to the request received from Merck-Medco to convert *John's* retail prescriptions to our mail service pharmacy.

---

COPYRIGHT AND LEGAL INFORMATION
USE OF INFORMATION

FIG. 11

| My Doctor Visit | Print The Kit |  |

> My Doctor Visit

What's Included
Medication history
Patient requests
Benefit information
Formulary quick guide
Prescription fax form Patient name: John- D.O.B. 07/29/1969 ▼

Benefit Information
This section reflects your plan's typical copay information for brand and generic medications.

For more detailed information about coverage and pricing for specific medications for the selected patient, click here to be taken to our prescription coverage and pricing area.

✉ plan coverage through mail service pharmacy
👤 plan coverage at retail pharmacy

| Days' supply: |
|---|
| Home delivery ✉ — You can obtain up to 90 days supply when using the mail service. |
| Retail 👤 — You can obtain up to 21 day supply when purchasing medication from a participating pharmacy. |

| Copay for brand-name medications: |
|---|
| Home delivery ✉ — When using the mail service, your copay for a brand name medication is $10.00 for most medications. Other specific drug classifications have a different copay. |
| Retail 👤 — When using your card at a participating pharmacy, your copay for a brand name medication is $10.00 for most medications. Other specific drug classifications have a different copay. |

| Copay for generic medications: |
|---|
| Home delivery ✉ — When using the mail service, your copay for a brand name medication is $0.00 for most medications. Other specific drug classifications have a different copay. |
| Retail 👤 — When using your card at a participating pharmacy, your copay for a generic medication is $6.00 for most medications. Other specific drug classifications have a different copay. |

| Copay for brand-name medications when a generic is available: |
|---|
| Home delivery ✉ — When using the mail service, your copay for a brand name medication when a generic is available is $10.00 for most medications. Other specific drug classifications have a different copay. |
| Retail 👤 — When using your card at a participating pharmacy, your copay for brand-name medication when a generic is available is $10.00 for most medications. Other specific drug classifications have a different copay. |

COPYRIGHT AND LEGAL INFORMATION
USE OF INFORMATION

FIG. 12

| My Doctor Visit | Print The Kit | (?) |

> My Doctor Visit

Patient name: John- D.O.B. 07/29/1969 ▼

What's Included
- Medication history
- Patient requests
- Benefit information
- Formulary quick guide
- Prescription fax form

Formulary quick guide

This convenient, easy-to-understand quick guide includes most of the commonly prescribed medications preferred by your health plan. This guide is a useful tool in helping you and your doctor to maximize your health plan benefits.

ANTI - INFECTIVES
(Antibiotics/Antifungals)

Oral Antifungals
| | |
|---|---|
| $ | + griseofulvin, ultramicrosize |
| $ | + nystatin |
| $$ | Grifulvin V |
| $$ | Mycelex |
| $$$$ | Diflucan |
| $$$$ | Fungizone |
| $$$$⊕ | ketoconazole (Nizoral) |
| $$$$ | Lamisil |
| !!!! | Ancobon |
| !!!! | Sporanox |

Oral Cephalosporins
| | |
|---|---|
| $ | + cephalexin monohydrate |
| $ | + cephradine |
| $$ | + cefaclor |
| $$$ | Ceftin |
| $$$ | Lorabid |
| $$$ | Omnicef |
| $$$ | Suprax |
| $$$ | Vantin |

Oral Penicillins
| | |
|---|---|
| $ | + amoxicillin trihydrate |
| $ | + ampicillin trihydrate |
| $ | + penicillin v potassium |
| $$ | Amoxil |
| $$ | Amoxil |
| $$$ | Augmentin |
| $$$ | + dicloxacillin sodium |

Oral Sulfas
| | |
|---|---|
| $ | + erythromycin |
| $ | Gantrisin |
| $ | + sulfamethoxazole /trimethoprim |
| $$ | + sulfisoxazole |
| !!!! | + sulfadiazine |

Vaginal Antifungals
| | |
|---|---|
| $$ | Diflucan |
| $$ | + nystatin |
| $$$ | Terazol |
| $$$ | Monistat 3 |

CARDIOVASCULAR
(Blood Pressure/Heart/Cholesterol)

ACE Inhibitors/Combinations
| | |
|---|---|
| $ | + captopril |
| $ | + hctz/propranolol HCL |
| $ | + hydralazine HCL/HCTZ |
| $ | + reserpine/HCTZ |
| $$ | PCE |
| $$ | Zithromax |
| $$$ | Biaxin |
| $$$ | Biaxin XL |

Antilipidemics
| | |
|---|---|
| $$$ | Cipro |
| $$$ | Cipro |
| $$$ | Noroxin |
| $$$$ | Floxin |

KEY
| | |
|---|---|
| $ | = Lowest Relative Cost |
| !!!! | = Highest Relative Cost |
| + | = Use Generic (Brand nonformulary) |
| ⊕ | = Use Generic (Brand nonformulary) |

Relative Cost Index is a relative indication of the cost to the payer for medications. It does not reflect costs incurred by patients or dispensers. More dollar signs indicate a more costly agent to the plan.

FIG. 13

<<Patient Name>>'s Drug Information /1402

As of: <<Date>> /1404   Member ID: 999999999 /1405
Date of Birth: <<Date>>   Group #: 999999999
                    \1406                    \1407

1403
(Form Content)
Merck-Medco would like to support your efforts to keep your patients healthy by providing patient specific prescription information such as medication histories. And though we know you can not always consider cost when prescribing using the information below as a guide can help make the drugs you want to prescribe more affordable for you patient.

*Mail envelope icon* /1408 prescription you filled through your mail-service pharmacy
*Mail person icon* prescription you filled at a retail (walk-in) pharmacy

| Medication History: | | | | | |
|---|---|---|---|---|---|
| This list is comprised of prescriptions filled at our home delivery pharmacy and at the patient's retail pharmacy. | | | | | |
| Prescription (Rx) number; Medication name; strength | 1410 Rx filled at | 1411 Date filled | 1412 Quantity | Days supply | Days past refill date |
| #123456789012 Cholestyramine 250mg | 👤 | <<10/13/00>> | <<30>> | <<30>> | <<72>> ~1414 |
| 1409 | 👤 | <<8/1/00>> | <<30>> | <<30>> | |
| <<Lotensin>> | ✉ | <<09/10/00>> | <<180>> | <<90>> | <<0>> |
| | | | | 1413 | |
| | | | | | |
| | | | | | |
| | | | | | |

| Patient Savings Opportunities: |
|---|

Your patient can often save using our home delivery mail service pharmacy. For ongoing prescriptions, please consider:
→ Writing a 14-day prescription to reset your patient's immediate needs through a retail pharmacy.
→ Writing up to a 90-day prescription for our home delivery pharmacy.
Send the prescription to us today by taping x to our *Prescription Authorization Form* and faxing it to us.

Your patient can save using the generic equivalent:
Please consider prescribing the generic version of medications where appropriate so your patient may enjoy additional savings.

| Patient Requests: |
|---|
| While communicating with Merck-Medco, your patient asked us to contact you to request: |
| • New prescriptions for <<drug name, drug name and drug name>> medications he/she are currently taking. 1415
✓ Action: If you have not already done so, please respond to the renewal requests received from Merck-Medco on your patient's behalf  1416 |
| • Pharmacy drugs for <<drug name and drug name>> to our mail service pharmacy.
✓ Action: If you have not already done so, please respond to the requests received from Merck-Medco to convert your patient's retail prescriptions to our mail service pharmacy. |

Benefit Information:* 1417

| | Maximum days supply | Generic co-payment | Brand co-payment |
|---|---|---|---|
| Home delivery (mail service) | <<90>> | <<$10>> | <<$16>> |
| Retail (walk-in) | <<30>> 1418 | <<$7>> 1419 | <<$13>> 1420 |

*This information is meant to serve as a general guide. The co-payment for certain medications may vary.

FIG. 14

| My Doctor Visit | Add'l Fax Form    Print The Kit   ? |
|---|---|

> My Doctor Visit

Patient name: John- D.O.B. 07/29/1969 ▼

| What's Included |
|---|
| Medication history |
| Patient requests |
| Benefit information |
| Formulary quick guide |
| Prescription fax form |

☐ Prescription Fax Form

For you and your doctor's convenience, you may bring the prescription authorization form to your doctor visit to request new prescriptions. This form can be completed and faxed to our mail service pharmacy by your doctor.

Below is an example of the prescription authorization form. Do not attempt to print from this page. The prescription authorization form is part of the My Doctor Visit kit which can be printed by clicking the "Print The Kit" button above.

---

MMRx • Logo • FPO                                       Prescription Fax Form

Please fully complete steps 1 to 4 below to help ensure timely processing of your patient's prescription
Questions: Call Customer Service at (1-888-327-0791)

BAR CODE FPO

STEP 1   Fill in both the Subscriber and the Patient information below.
Prescription Drug
Card Member #:
(Usually different than the health plan ID #)

Subscriber Information (card holder):

Name:(First) _____ (Last) _____

Address: _____

City _____ State _____ Zip Code _____ Phone _____

Patient Name:(First) _____ (Last) _____ DOB: _____

| STEP 2:<br>Confirm your office's secure fax #.<br>Check the box to indicate a change,<br>and write in the correct #.<br><br>☐ New fax #:<br><br>STEP 3:<br>Complete for new patients or for<br>patients with changes in health.<br>*Please check all that apply:*<br>Allergies:<br>☐ None  ☐ Sulfa   ☐ Penicillin<br>☐ Aspirin ☐ Codeine ☐ Iodine<br>Medical Conditions:<br>☐ Heart ☐ Asthma  ☐ High B.P.<br>☐ Ulcer ☐ Glaucoma<br>Other _____ | STEP 4  Please tape the prescription from your prescription pad here (Most patients can receive up to a 90-day supply and 4 refills.)<br><br>TAPE PRESCRIPTION HERE<br><br>Please confirm you have included:<br><br>*On the form:*<br><br>• Subscriber's Drug Card Number<br><br>*On the prescription:*<br><br>• Patient's Full Name<br>• Patient's Date of Birth<br>• Date Prescription Written<br>• Your Signature |

FIG. 15

PATIENT ORIENTED POINT OF CARE SYSTEM AND METHOD

FIELD OF THE INVENTION

The present invention generally relates to methods, systems and medium wherein a patient may provide, to a physician, patient specific information relating to a patient to assist the physician in providing medical/health care to the patient.

BACKGROUND OF THE INVENTION

Health care costs represent a significant portion of the economic activity of the United States and continue to rise at a faster rate than the inflation rate of the overall economy. A contributing factor of the ever increasing health care costs is pharmacy care costs, which are increasing even faster than the health care costs. In order to reduce the costs of care, physicians have been under increasing pressure to be more efficient in patient care. In the area of the pharmacy care, this means physicians are required to understand and analyze a patient's pharmacy care history completely and efficiently.

There have been a number of proposed approaches in presenting patient pharmacy care history to information physicians. One such conventional system using a computerized system, a prescription creation screen 39, is illustrated in FIG. 1 and described in U.S. Pat. No. 5,845,255 to Mayaud incorporated herein by reference. The creation screen 39 includes an array of buttons that can be activated by a user (e.g., a physician). In discussing various buttons of the prescription creating screen 39, near the top of screen 39 is a patient features bar 40 below which a prescription features bar 42 coordinates features necessary to review current therapy and order changes in treatment, or to order new treatment, for a selected patient. A prescription history zone 43 extends across the middle of the screen, the lower screen portion contains a prescribing zone 44, and a screen title 45 appears at the top of the screen.

Patient features bar 40 comprises a Select Patient button 46, a selected patient indicator 48, in this case Mary Harrington, a patient Problems button 50 and a patient Allergies button 52. Beneath Problems button 50 are displayed Mary Harrington's currently active problems 51 or conditions, shown here as pharyngitis and bronchitis. Beneath Allergies button 52 are displayed Mary Harrington's known allergies. Pressing or otherwise activating Problems button 50 or Allergies button 52 access a remote database for the patient's history and, opens a window or screen listing problems or allergies from which a physician, or other professional users, can select new problems or allergies to add to Mary Harrington's record, or delete ones that are no longer active. Optionally, system-provided problem or allergy libraries may be organized into multiple lists with button 50 or 52, respectively, opening a list selection box as a preliminary to displaying a selected problem or allergy list.

Prescription features bar 42 comprises an Rx History button 54, an Rx Options button 56, an Updating indicator 58, an Rx Info button 60 and a Renew Rx button 62.

Prescription history zone 43 displays those historical prescription details that may be relevant to a current prescription and has a Condition field 64, a Drug field 66, a Size field 68 a Dosing field 70, a generic flag 72, an Expires field 74 and a Mine field 76, in which the various characteristics of patient Mary Harrington's previous prescriptions are listed.

Prescribing zone 44 comprises three active buttons, New Rx button 78, Send Rx button 80 and Close button 82, below which extends a prescribing header bar 84 which contains field identifiers for data entry of a full complement of prescription details. Available prescription detail fields comprise a Condition field 86, a Drug field 88, a Generic field 90, a Form field 92, a Size field 94, a Route field 96, an Amt (Amount) field 98, a Refill field 100, a Dosing field 102 and an Expires field 104.

Multiple lines of the selected patient's prescription history are listed in patient history zone 43 in the middle of the screen for review by the physician-user, and possible renewal, with scrolling or paging of extensive histories. Depending upon the patient's previous whereabouts and service providers, individual lines may come from multiple remote sources.

Prescribing zone 44, lowers down prescription creation screen 39, allows a physician user to select and prescribe drugs and dosages, for the selected patient, in this case Mary Harrington, and to transmit the created prescription by activating the Send Rx button 80, externally across a data network to other interested and authorized parties for prescription fulfillment block 55, patient record updating arrow 57 and the like. Send Rx button 80 can also output the prescription to print or storage.

Select Patient button 46 brings up a patient selection screen for selecting a different patient from one or more lists. Select Patient button 46 draws up a "Today's Patients" list or whichever patient list the user last selected from, or a default, user-selected patient list, and provides the options of selecting a new patient from alternative patient lists.

Problems button 50 brings up a patient problem history information screen in which a historical record of the patient's individual symptoms and diagnoses is listed and to which new problem reports can be posted. To maintain data integrity, and as a legal safeguard, historical information is not editable but may be supplemented, for example by reporting the subsequent status of a problem as (still) active or inactive. Any such additions to the record are stamped with the identity of the reporting physician, providing valuable elements of a treatment decision-making audit trail.

The patient's drug-related allergies, or drug reactions, are brought up in possibly editable form (screen not shown) by activating an Allergies button 52 and may be automatically updated, if desired by adding newly reported drug reactions and allergies, arrow 51. Desired personal or drug records relevant to possible allergies of this patient may be summoned from a host computer facility, which may in turn call on a remote database data-retrieval network block for records or record elements.

Rx History button 54, scrolls, drops down, or otherwise accesses any additional patient history lines beyond what will fit in prescription history zone 43 and may introduce vertical or horizontal scroll bars, or both, into zone 43, enabling the user to display any desired section of a patient's prescription history in zone 43 with the top line of the history highlighted. Any desired prior prescription line displayed in zone 43, can be highlighted by clicking or pressing on it.

A highlighted prior prescription can be automatically renewed by clicking or pushing a Renew Rx button 62. Typically, prescription creation screen 39 opens with the most recent prescription highlighted for possible renewal. Activating Renew Rx button 62 posts a highlighted prior prescription into prescribing zone 44 for automatic renewal, after editing, if desired. Renewal of any prior prescription can thus be effected in as few as two user steps by pressing Renew Rx 62 to post a highlighted previous prescription to prescribing zone 44 and completing a prescription in a single step from there. If desired option buttons such as Renew and Send Last Prescription or Renew All Active Prescriptions can be added. Pressing header buttons Condition 64, Drug 66, or Expires 74 causes the drug history display to be sorted by the selected header enabling the prescription history to be evaluated according to a particular parameter.

Because prescription creation screen 39 is complex and elaborate, a physician must invest time to learn and use it. Should there be more than one type of screen (e.g., each insurance carrier may have its own screen), the physician has to invest more time to learn them all. Due to these and other shortcomings, instead of assisting physicians in streamlining their practices, the conventional computerized systems may actually cause the physicians to be inefficient. FIG. 2 is an illustration of a conventional computerized system requires a physician to purchase/license not only software packages to run the screen(s) but other communication equipment as well.

In particular, the left hand side of FIG. 2 shows an arrangement of services and devices that provide a downstream flow of data and communication resources to users of the conventional system. The right hand side shows sources from which desired data and data elements may be drawn and pathways for those data to reach the user. The flow is marshalled by a centrally depicted host computer.

Shown schematically in FIG. 2, are a number of user interface devices 200 and a desktop computer 201 communicating via any of a variety of communication services 202, through a gateway-router 204 with a host computer facility 206. FIG. 2 depicts schematically how a group or pool of users working with interface devices 200 or computers 201 running the screen 39, can be serviced by host computer facility 206.

Interface devices 200 are depicted as small form factor, handheld devices, or PDA's, communicating wirelessly over a WAN, a proprietary wireless service, or a cellular digital packet data service, or the like. Desktop computer 201, which may be a portable, notebook or other higher form factor computer, connected to communications gateway-router 204 via a local area network labeled LAN.

As shown above, the conventional computerized system requires physicians to purchase computer(s) and communication equipment, which may be different for each insurance carrier, in order to communicate with host computer facility 206, which may also be different for each insurance carrier. This requirement, rather than assisting physicians in understanding and analyzing patients' pharmacy care history, may actually hinder such activity and impose additional capital expenditures on physicians.

SUMMARY OF THE INVENTION

Computer-assisted methods, systems and mediums of the present invention overcome, among others, the shortcomings of the above-described conventional systems and efficiently provide, to physicians, information relating to patients. One of the methods comprises the steps of collecting a prescription history that includes information relating to one or more prescriptions issued to the patient and a prescription purchase history that includes information relating to one or more purchases made by the patient in accordance with the one or more prescriptions. The method also includes the steps of storing the prescription history and prescription purchase history of the patient into a database and accessing, by the patient, the database for the stored prescription history and prescription purchase history of the patient. The method also includes the steps of retrieving the prescription history and prescription purchase history and communicating, by the patient, the retrieved prescription history and prescription purchase history to the physician in order to assist the physician in providing medical services to the patient.

In particular, the step of communicating by the patient may further optionally comprise the steps of printing information relating to the retrieved prescription history and prescription purchase history, and presenting, by the patient, the printed information to the physician. The printing step may further comprise the steps of combining the information relating to the retrieved prescription history and prescription purchase history and formatting the combined information into a form presentable the physician. The communicating step by the patient may also comprise the step of sending, by the patient, to the physician an electronic message that contains the retrieved prescription history and prescription purchase history. The electronic message can be a PDA message.

In other aspects of the invention, the method may also include the step of collecting the prescription history and prescription purchase history when the one or more prescriptions are issued by different physicians, or when drugs prescribed in the prescriptions are purchased from different pharmacists. The different pharmacists include at least one pharmacy that delivers purchased drugs via standard delivery mechanisms or other means, such as mail or retail.

The method may also include the step of storing to the database information relating to pharmacy benefits for the patient and information relating to a drug formulary preferred by a pharmacy insurance carrier of the patient. In such an embodiment, the method may further include the steps of accessing, by the patient, the database for the stored information relating to pharmacy benefits for the patient and the preferred drug formulary, and retrieving the information relating to pharmacy benefits for the patient and the preferred drug formulary. The embodiment may also include the steps of printing the information relating to pharmacy benefits for the patient and the preferred drug formulary, printing information relating to the retrieved prescription history and prescription purchase history, and presenting, by the patient, the printed information to the physician. The printing step may comprise the steps of combining the information relating to pharmacy benefits for the patient and the preferred drug formulary with information relating to the retrieved prescription history and prescription purchase history, and formatting the combined information into a form presentable the physician.

In another method of providing, to a physician, information relating to a patient, the method may comprise the steps of collecting a prescription history that includes information relating to one or more prescriptions issued to the patient and a prescription purchase history that includes information relating to one or more purchases (including prescription and/or non-prescription related products) made by the patient in accordance with the one or more prescriptions, over-the-counter medications including herbal and/or natropathic medications, storing the prescription history and prescription purchase history of the patient into a database, and storing to the database information relating to pharmacy benefits for the patient and information relating to a drug formulary preferred by a pharmacy insurance carrier of the patient. The method may also include the steps of accessing, by the patient, the database for the stored information, retrieving the accessed information, and communicating, by the patient, the retrieved information to the physician in order to assist the physician in providing medical services to the patient.

More specifically, the step of communicating by the patient may further comprise the steps of printing the retrieved information and presenting, by the patient, the printed information to the physician. The printing step may comprise the steps of combining the retrieved information, and formatting the combined information into a form presentable the physician. The step of communicating by the patient may comprise the step of sending, by the patient, to the physician an electronic message that contains the retrieved information. The electronic message can be a PDA message.

The method may further comprise the step of collecting the prescription history and prescription purchase history when the one or more prescriptions are issued by different physicians or when drugs prescribed in the one or more prescriptions are purchased from different pharmacists. The different pharmacists include at least one pharmacy that delivers the prescriptions via, for example, mail or other means.

A computer assisted system, for providing to a physician information relating to a patient, includes means for collecting a prescription history and a prescription purchase history. The prescription history includes information relating to one or more prescriptions issued to the patient. The prescription purchase history includes information relating to one or more purchases made by the patient in accordance with the one or more prescriptions. The system may also include a means for storing the prescription history and prescription purchase history of the patient into a database and means for accessing, by the patient, the database for the stored prescription history and prescription purchase history of the patient. The system may further include means for retrieving the prescription history and prescription purchase history, and means for communicating, by the patient, the retrieved prescription history and prescription purchase history to the physician in order to assist the physician in providing medical services to the patient.

In particular, the means for communicating by the patient may also comprise means for printing information relating to the retrieved prescription history and prescription purchase history, to thereby allow the patient to present the printed information to the physician. The printing means may further include means for combining the information relating to the retrieved prescription history and prescription purchase history, and means for formatting the combined information into a form presentable the physician. The means for communicating by the patient may also include means for sending, by the patient, to the physician an electronic message that contains the retrieved prescription history and prescription purchase history. The electronic message can be, for example, a standard Personal Digital Assistant (PDA) message, PC message, pager message, fax message or other message delivered to a platform that is capable of receiving an electronic message.

The system may further comprise means for collecting the prescription history and prescription purchase history when the one or more prescriptions are issued by different physicians or means for collecting the prescription history and prescription purchase history when drugs prescribed in the one or more prescriptions are purchased from different pharmacists. The different pharmacists include at least one pharmacy that delivers purchased drugs via mail. The system also includes means for storing to the database information relating to pharmacy benefits (e.g., medical insurance coverage) for the patient and information relating to a drug formulary preferred by a pharmacy insurance carrier of the patient. In this embodiment as well as other embodiments, the system may also include means for accessing, by the patient, the database for the stored information relating to pharmacy benefits for the patient and the preferred drug formulary, and means for retrieving the information relating to pharmacy benefits for the patient and the preferred drug formulary. This system may also include a means for printing the information relating to pharmacy benefits for the patient and the preferred drug formulary and information relating to the retrieved prescription history and prescription purchase history, to thereby allow the patient to present the printed information to the physician. The printing means may comprise means for combining the information relating to pharmacy benefits for the patient and the preferred drug formulary and information relating to the retrieved prescription history and prescription purchase history, and means for formatting the combined information into a form presentable to the physician.

In another embodiment of the system of providing, to a physician, information relating to a patient of the present invention, the system comprises means for collecting a prescription history that includes information relating to one or more prescriptions issued to the patient and a prescription purchase history that includes information relating to one or more purchases (including prescription and/or non-prescription related products) made by the patient in accordance with the one or more prescriptions, means for storing the prescription history and prescription purchase history of the patient into a database, and means for storing to the database information relating to pharmacy benefits for the patient and information relating to a drug formulary preferred by a pharmacy insurance carrier of the patient. The system may also include means for accessing, by the patient, the database for the stored information, means for retrieving the accessed information, and means for communicating, by the patient, the retrieved information to the physician in order to assist the physician in providing medical services to the patient.

In particular, the means for communicating by the patient may also comprise means for printing, by the patient, the retrieved information, to thereby allow the patient to present the printed information to the physician. The printing means may further comprise means for combining the retrieved information, and means for formatting the combined information into a form presentable the physician. The means for communicating by the patient may also comprise means for sending, by the patient, to the physician an electronic message that contains the retrieved information. The electronic message can be a PDA message.

In another aspect of the present invention, the system may further include means for collecting the prescription history and prescription purchase history when the one or more prescriptions are issued by different physicians or means for collecting the prescription history and prescription purchase history when drugs prescribed in the one or more prescriptions are purchased from different pharmacists. The different pharmacists include at least one pharmacy that delivers purchased drugs via mail.

The preset invention also includes a computer readable medium having instructions being executed by one or more computers, the instructions directing the one or more computers for providing to a physician information relating to a patient. The instructions comprising implementation of the steps of collecting a prescription history that includes information relating to one or more prescriptions issued to the patient and a prescription purchase history that includes information relating to one or more purchases made by the patient in accordance with the one or more prescriptions, storing the prescription history and prescription purchase history of the patient into a database, and accessing the database for the stored prescription history and prescription purchase history of the patient. The instructions may also include the steps of retrieving the prescription history and prescription purchase history, and communicating the retrieved prescription history and prescription purchase history to the physician in order to assist the physician in providing medical services to the patient. The accessing step and the communicating step are advantageously initiated by the patient.

More specifically, the step of communicating by the patient may also comprise the step of printing information relating to the retrieved prescription history and prescription purchase history, to thereby allow the patient to present the printed information to the physician. The printing step may also comprise the steps of combining the information relating to the retrieved prescription history and prescription purchase history, and formatting the combined information into a form presentable to the physician. The step of communicating by the patient may also comprise sending to the physician an electronic message that contains the retrieved prescription history and prescription purchase history. The electronic message can be a PDA message. In another aspect of the present invention, the medium may further include instructions relating to the step of collecting the prescription history and prescription purchase history when one or more prescriptions are issued by different physicians, or collecting the prescription history and prescription purchase history when drugs prescribed in one or more prescriptions are purchased from different pharmacists. The different pharmacists include at least one pharmacy that delivers purchased drugs via mail.

The medium may also include instructions relating to the steps of storing to the database information relating to pharmacy benefits for the patient and information relating to a drug formulary preferred by a pharmacy insurance carrier of the patient. In such an embodiment, the medium may also include instructions relating to the step of accessing the database for the stored information relating to pharmacy benefits for the patient and the preferred drug formulary; and retrieving the information relating to pharmacy benefits for the patient and the preferred drug formulary, wherein the accessing step is initiated by the patient. The medium may also include instructions relating to the steps of printing the information relating to pharmacy benefits for the patient and the preferred drug formulary and information relating to the retrieved prescription history and prescription purchase history, to thereby allow the patient to present the printed information to the physician. The printing step may further comprise the steps of combining the information relating to pharmacy benefits for the patient and the preferred drug formulary and information relating to the retrieved prescription history and prescription purchase history, and formatting the combined information into a form presentable to the physician.

Another embodiment of the present invention includes a computer readable medium having including instructions being executed by one or more computers. The instructions direct the one or more computers for providing, to a physician, information relating to a patient. The instructions comprise implementation of the steps of collecting a prescription history that includes information relating to one or more prescriptions issued to the patient and a prescription purchase history that includes information relating to one or more purchases made by the patient in accordance with the one or more prescriptions, storing the prescription history and prescription purchase history of the patient into a database, and storing to the database information relating to pharmacy benefits for the patient and information relating to a drug formulary preferred by a pharmacy insurance carrier of the patient. The medium may also include instructions relating to the steps of accessing the database for the stored information, retrieving the accessed information, and communicating the retrieved information to the physician in order to assist the physician in providing medical services to the patient, wherein the assessing step and the communicating step are initiated by the patient.

More specifically, the step of communicating by the patient may also comprise the steps of printing, by the patient, the retrieved information, to thereby allow the patient to present the printed information to the physician. The printing step comprises the steps of combining the retrieved information, and formatting the combined information into a form presentable the physician. The step of communicating by the patient may comprise sending, by the patient, to the physician an electronic message that contains the retrieved information. Alternately, the patient may download this report to the physicians' computer and/or mobile device or to their own device (e.g., PDA, disk, key card, storage media, etc.)In another embodiment of the present invention, the medium may also include instructions relating to the steps of collecting the prescription history and prescription purchase history when the one or more prescriptions are issued by different physicians or collecting the prescription history and prescription purchase history when drugs prescribed in the one or more prescriptions are purchased from different pharmacists. The different pharmacists include at least one pharmacy that delivers purchased drugs via mail.

There has thus been outlined, rather broadly, the features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Other features of the present invention will be evident to those of ordinary skill, particularly upon consideration of the following detailed description of the preferred embodiments.

Notations and Nomenclature

The detailed descriptions which follow may be presented in terms of program procedures executed on computing or processing systems such as, for example, a stand-alone computing machine, a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those that may require physical manipulations of physical quantities (e.g., storing prescription history information into a database). Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

BRIEF DESCRIPTION OF THE DRAWINGS

The detailed description of the present application showing various distinctive features may be best understood when the detailed description is read in reference to the appended drawing in which:

FIG. 4 is a diagram illustrating an example Web page of a "My" page presented in FIG. 3;

FIG. 5 is a diagram illustrating an example Web page of a "Prescription" page of FIG. 3;

FIG. 6 is a diagram illustrating an example Web page of a "My Health" page of FIG. 3;

FIG. 8 is a diagram illustrating an example Web page of a "My Store" page of FIG. 3;

FIG. 9 is a diagram illustrating an example Web page of a "My Doctor Visit" page of FIG. 3;

FIG. 10 is a diagram illustrating an example Web page of a "Medication History" page of FIG. 3;

FIG. 11 is a drawing illustrating an example Web page of a "Patient Request" page of FIG. 3;

FIG. 12 is a drawing illustrating an example Web page of a "Benefit Information" page of FIG. 3;

FIG. 13 is a drawing illustrating an example Web page of a "Drug Formulary" page of FIG. 3;

FIG. 14 is a drawing illustrating an example Doctor Kit print;

FIG. 15 is a drawing illustrating an example Web page of a "Prescription Fax" page;

DETAILED DESCRIPTION OF THE INVENTION

Figure 1:
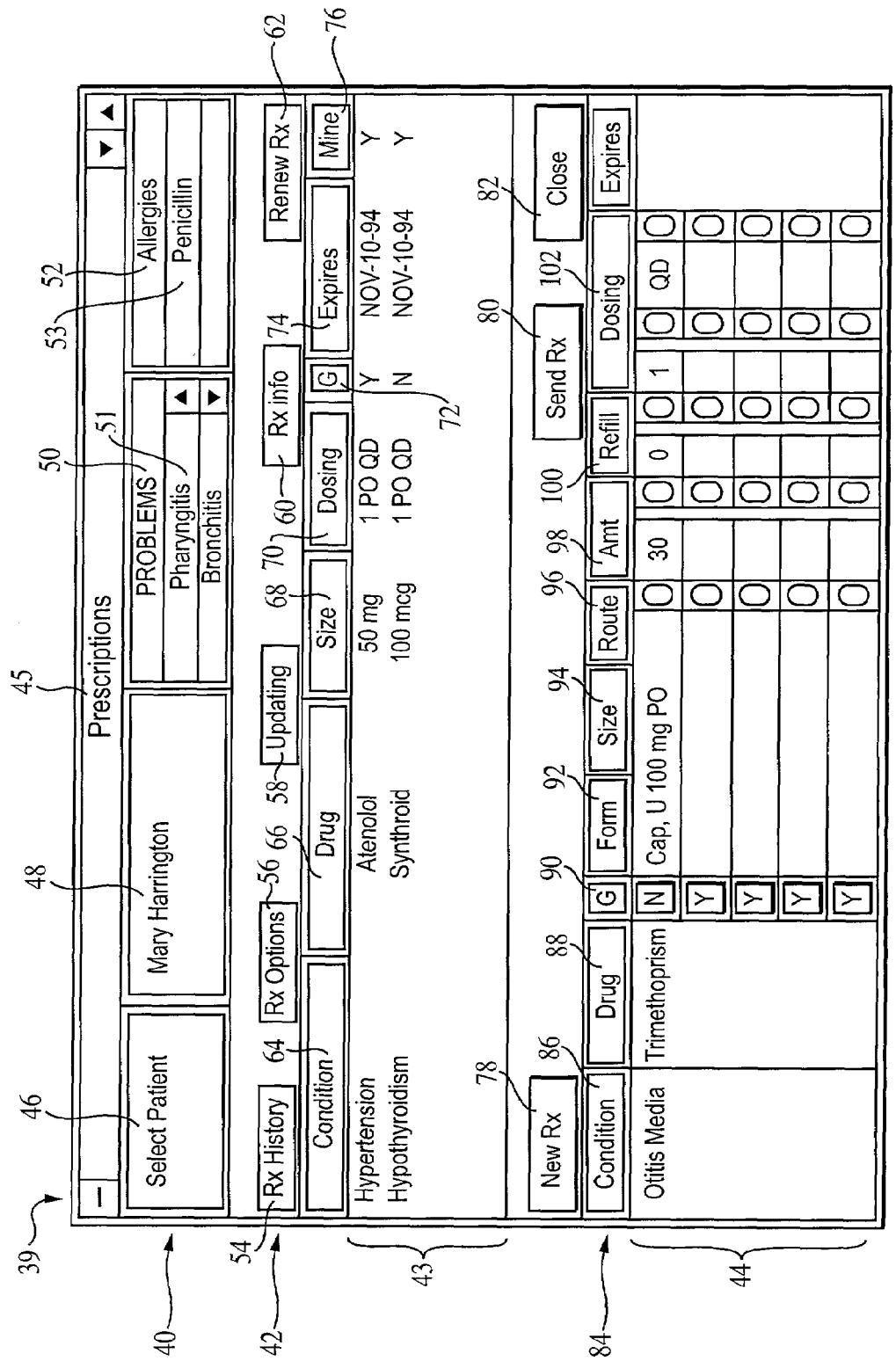
FIG. 1 is a drawing illustrating a conventional, prior art prescription creation screen.
Figure 2:
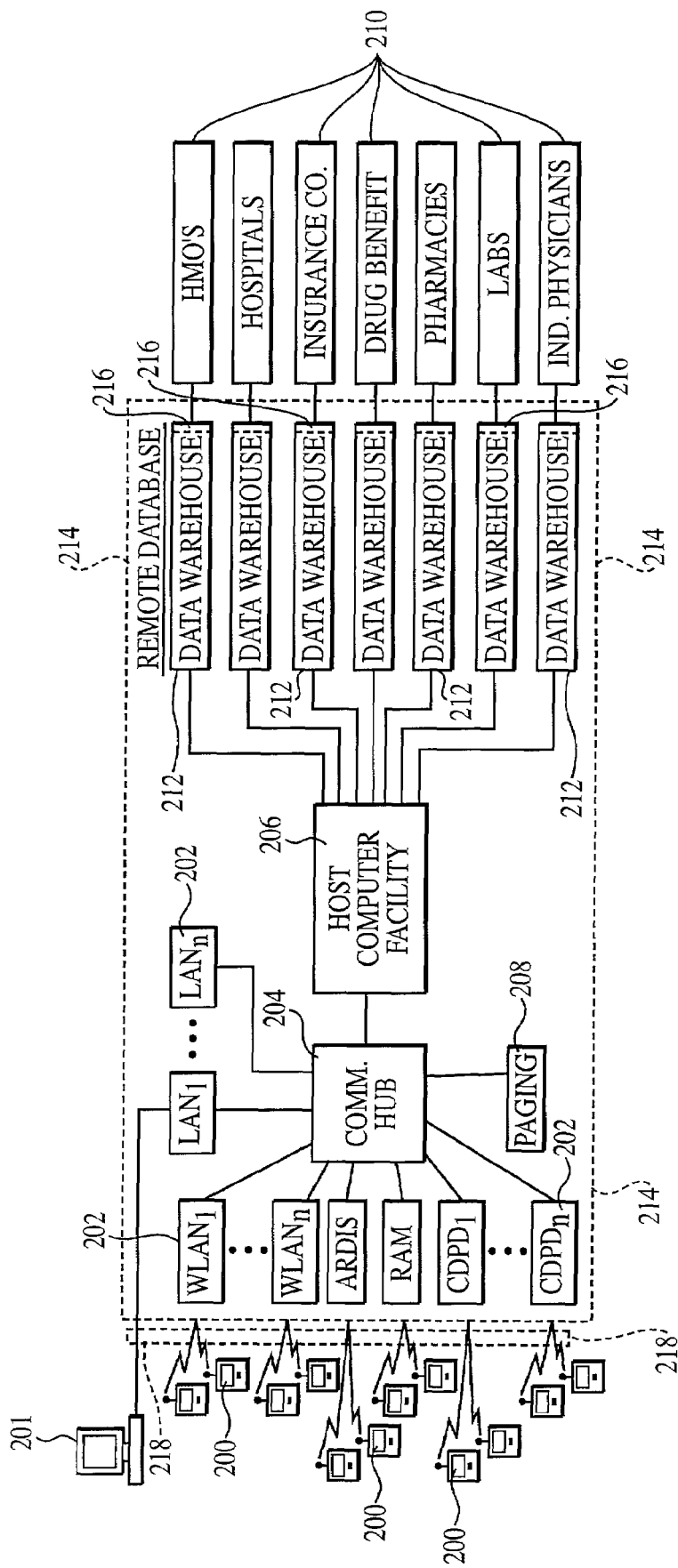
FIG. 2 is a schematic drawing illustrating a downstream flow of data and communication resources of the conventional, prior art prescription creation system.

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

Various embodiments of the present invention bring together patient specific, patient consented, up-to-date and timely information (e.g., real-time) in a convenient low-cost methodology to be easily accessible by physicians. In particular, some embodiments of the present invention are configured to allow a patient, who is scheduled to visit a physician, to retrieve his/her patient specific information from a database and print, or forward electronically, the retrieved information to the physician. It should be noted that, although embodiments of the present invention are described as providing information to physicians, providing information to other health care providers (e.g., an osteopath or pharmacist) is also contemplated within embodiments of the present invention.

The patient specific information includes one or any combination of the following sets of information: 1. past prescriptions issued to the patient by either the treating physician or other physicians; 2. whether or not the prescribed drugs have been purchased by the patient; 3. when the prescribed drugs were purchased; 4. The quantity of prescribed drugs purchased; 5. The number of days past from a refill date when a prescription has not been refilled; 6. insurance benefit information of the patient; 7. covered drug formulary, etc. The present invention provides an efficient way to present the patient specific information to the physician because it gives the full description of the patient's (e.g., prescription) history, including an indication of compliance by the patient. The physician can also consider the insurance benefit information which helps the patient to reduce drug expenditure. Unlike conventional systems, the physician is not required to obtain consent from the patient to receive the patient specific information, because the information presented to the physician is considered to be released by the patient with consent. It also saves the physician, patient, and pharmacy time as they do not have to revisit formulary or after prescriptions have been written by the physician, because the formulary information, and benefit issues is presented to the physician at the time or point of care.

Figure 3:
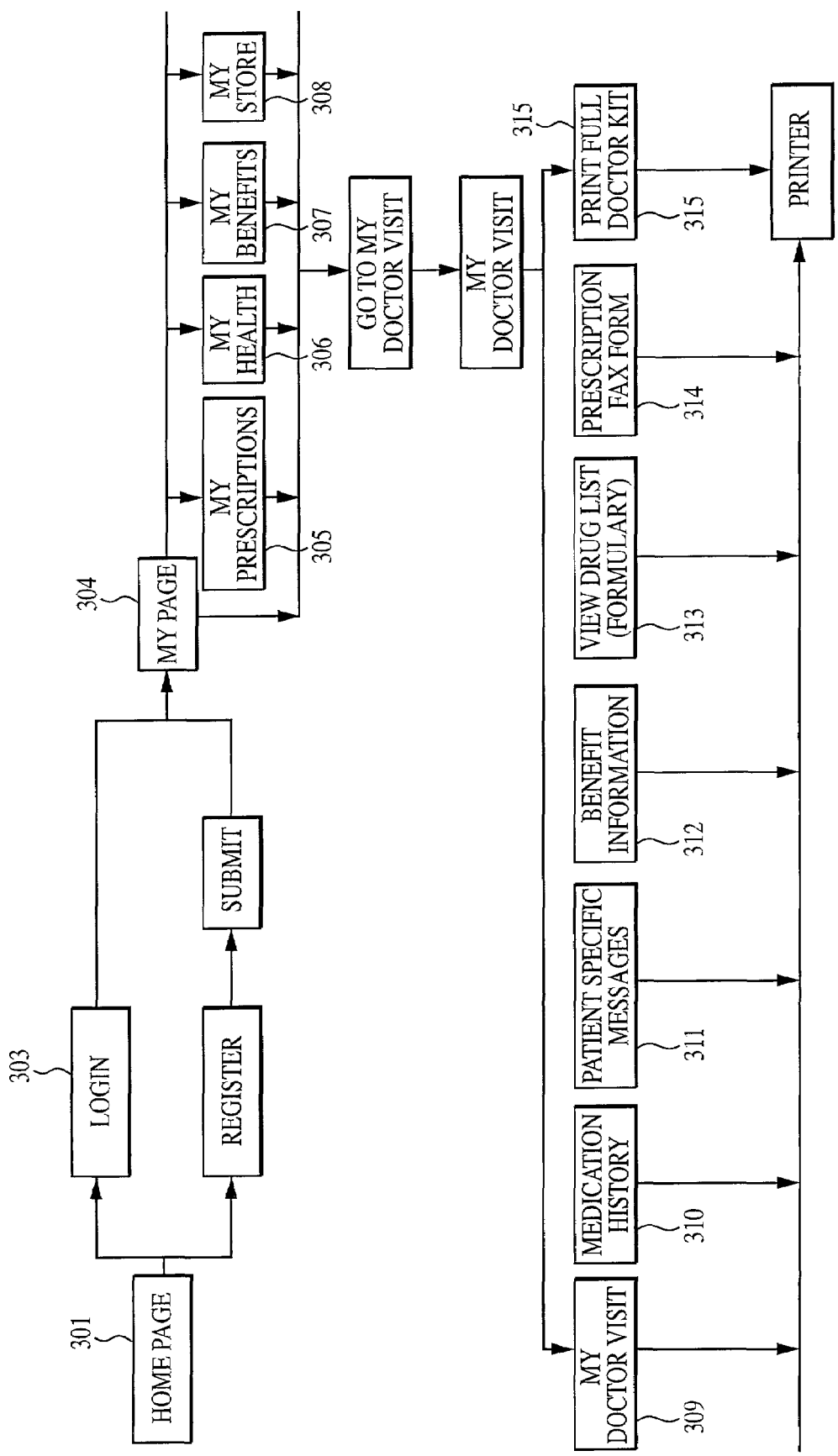
FIG. 3 is a flowchart illustrating a set of Web pages for example embodiments of the present invention.

The patient can access the patient specific information by visiting a Web site, via the Internet, that includes a number of Web pages, examples of which are illustrated in FIGS. 4-13. (The patient can also visit the Web site for refill, renewal or consent.) A summary of these example Web pages is graphically illustrated in FIG. 3. As shown in FIG. 3, the Web site includes the following example Web pages: a "Home" page 301, a "Login" page 303, a "My" page 304, a "My Prescriptions" page 305, a "My Health" page 306, a "My Benefits" page 307, a "My Store" page 308. Each of these Web pages provides an option (e.g., a button) that allows the patient to access a "My Doctor Visit" page 309. In turn, from the "My Doctor Visit" page 309, the patient can access any of the following Web pages: a "Medication History" page 310, a "Patient Specific Messages" page 311, a "Benefit" page 312, a "View Drug List (Formulary)" page 313, and a "Prescription Fax Form" page 314. A "Print Full Doctor Visit" option 315 is also provided to allow the patient to print the patient specific information. The Web pages can be written using, for example, HTML (Hypertext Markup Language), XML (extendable Markup Language) or the like. Each of the above-mentioned Web pages are described in detail below.

The "Home" page 301 is a Web page that displays general introductory information for the patient regarding the Web site. The "Home" page is configured such that the patient can access the rest of the Web pages of the Web site after a login process using the "Login" page 303. If the patient has not registered and cannot login, then the "Home" page is also configured to allow the patient to register and then login into the Web site.

Upon entering the Web site, the patient is presented with an introductory section explaining the benefits of a doctor kit (described below) as well as any other informational messages that is desired to be passed to the patient. A registered member is given a list of patients (e.g., other members of the patient's family) whose information can be viewed by other members of the same registered family. The caption for this list is "To begin, select a patient name:". If the current patient does not have access to view other patients, then just their names are available to choose from. In order for the patient to access full family view, they and their spouse/domestic partner need to grant family view. A member with this access set to "True" can view the doctor kit on a dependent under 18 or spouse. A spouse with this flag set can also view dependents under 18 and the member. The Web site can optionally be configured such that dependents under the age of 18 are unable to view this information on their parents or siblings.

After the patient selects a member from the list, the "My" page 304 appears. An example of the "My" page (for "John") is illustrated in FIG. 4. This page can optionally display a number of panes for displaying different types of information. In the example "My" page 304 shown in FIG. 4, three panes are illustrated: 1. Prescription Status pane 405; 2. Managing Health pane 407; and 3. Site Information pane 409. In the Prescription Status pane 405, information relating to refillable prescriptions (either for the patient only or for his/her family members) is displayed. In the Managing Health pane 407, information relating to the latest health research, news, etc. is displayed. In the Site Information pane 409, information relating to the Pharmacy Web site (e.g., new features) is displayed.

FIG. 5 illustrates an example of a "My Prescription" page 305, which displays prescription history of the patient and his/her family members who have been registered as belonging to one family. In this example page, prescriptions that have been issued to the patient and his/her family can be displayed one of three ways by selecting one of three buttons: 1. Prescriptions filled by mail prescription fillers 503; 2. Prescriptions filled at retail pharmacy stores 505; and 3. All prescriptions 507. The example list shows when the option for displaying Prescriptions filled by mail prescription fillers 503 is selected.

The example includes information relating to prescription number, prescribed drug name, prescribee's name, date received, date shipped and refills remaining. Each entry also includes the status thereof. In the example first entry of the list, the prescription number is 123456789012, the prescribed drug name is Metoprolol Tartrate Tabs, 50 mg tabs, the name of the patient is Gina, date received is Oct. 2, 2000, date shipped is Oct. 6, 2000 and refills remaining is 3.

FIG. 6 illustrates an example "My Health" page 306 which displays a number of panes that contain general health related information. This page displays four example topic panes: "Health Centers" 605, "Health Topics" 607, "Tools," 609 and "Resources" 611. In the "Health Centers" pane 605, one from many health centers can be selected (e.g., An Arthritis Center for information relating to arthritis, a Cardiovascular Center for information relating to blood circulation, etc.). The selected "Center" is displayed in "My Centers" field 612 which can be changed using an "edit" button 614.

Figure 7:
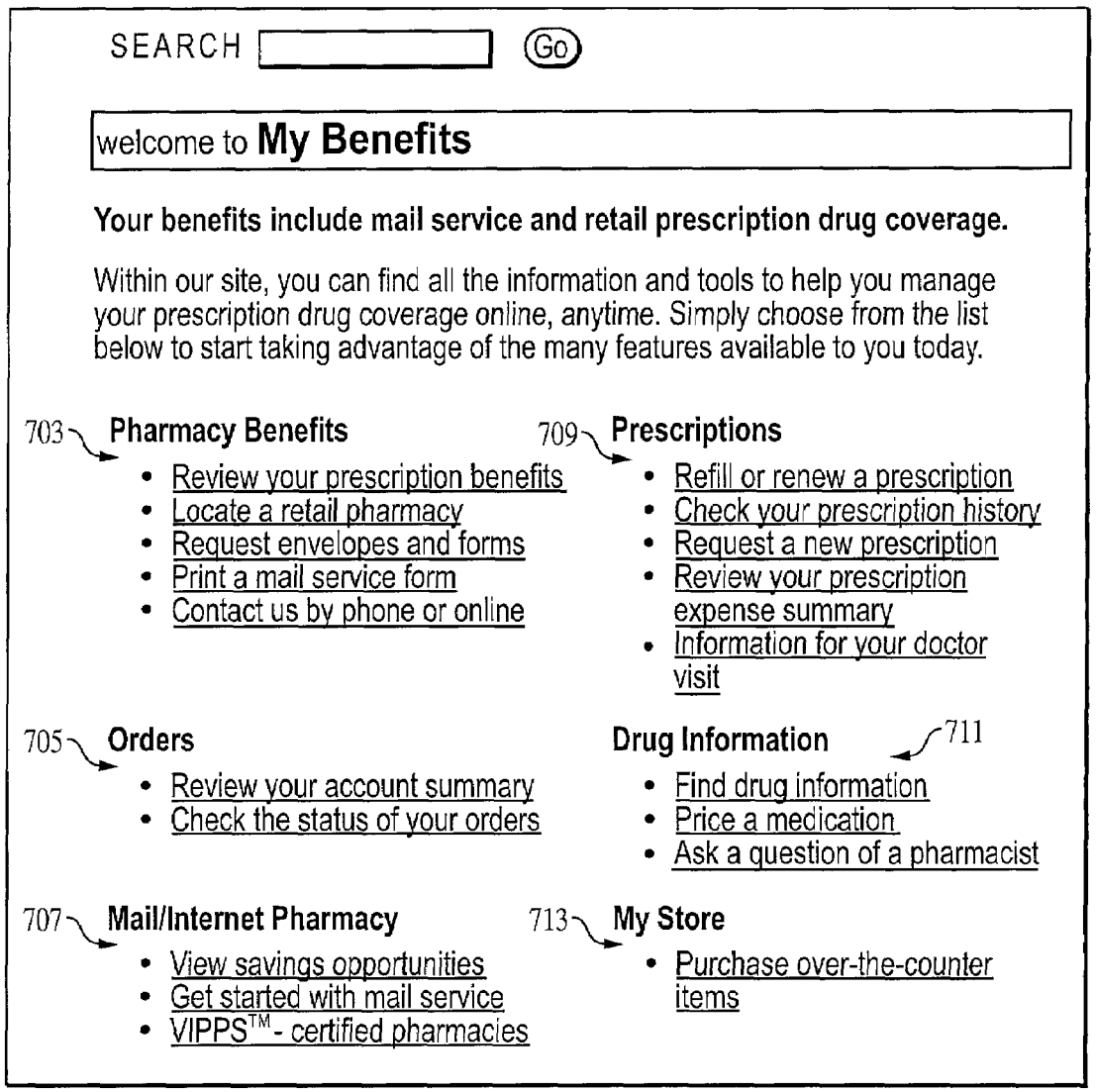
FIG. 7 is a diagram illustrating an example Web page of a "My Benefits" page of FIG. 3.

FIG. 7 illustrates an example "My Benefits" page 307 which includes a number of buttons that bring up, when selected, information relating thereto as follows:

A "Pharmacy Benefits" section 703 includes buttons for reviewing the patient's prescription benefits, locating a retail pharmacy, requesting envelopes and forms (for returning Rx or refill forms), printing a mail service form, and contacting the Pharmacist.

A "Prescriptions" section 709 includes buttons for refilling or renewing a prescription, checking the patient's prescription history, requesting a new prescription, reviewing the patient's prescription expense summary and receiving information for an upcoming visit.

An "Orders" section 705 includes buttons for reviewing the Patient's account summary and checking the status of the patient's orders.

A "Mail/Internet Pharmacy" section 707 includes buttons for viewing saving opportunities in purchasing prescribed drugs, starting with mail service (e.g., registrations).

A "Drug Information" section 711 includes buttons for finding information on a particular drug, displaying price of a medication, or asking questions to a pharmacist via e-mail.

A "My Store" section 713 includes a button for purchasing over-the-counter pharmaceutical and other products.

When the "My Store" button is selected, a "My Store" Web page is displayed. An example of the "My Store" Web page 308 is shown in FIG. 8. As shown in FIG. 8, the patient is allowed make purchases of various products—both pharmaceutical and non-pharmaceutical products.

From any of the above-described Web pages (except the "Home" and "Login" pages), the "My Doctor Visit" page, an example of which is illustrated in FIG. 9, can be accessed. The "My Doctor Visit" page is accessed by the patient when he/she is about to visit his/her physician. The following set of Web pages allows the patient to print patient-specific information so that the patient's physician can issue a new prescription based on, in part, the presented information.

As noted above, the patient can access information relating to his/her family members. Information relating to any member of the patient's family can be accessed by selecting a name from a name selection bar 903. The selected member information, then can be accessed by selecting one of a number of options in "What's Included" pane 905, which includes the following options: "Medication history," "Patient requests," "Benefit information," "Formulary quick guide," "Prescription fax e-mail form." These options, when selected, display a "Medication History" page 310, a "Patient Selected Message" page 311, a "Benefits" page 312, a "Formulary" page 313, and a "Prescription Fax Form" page 314, respectively.

The "Medication history" option illustrated in FIG. 9, when selected, causes a "Medication history" Web page to be displayed. An example of such a page is illustrated in FIG. 10. The main function of the page is to show the medication history of the members of the patient. The medication history includes information relating to a prescription number, medication name, strength of prescribed drugs, the method with which the prescription was filled (e.g., mail, local drug stores, etc.) the date on which the prescription was filled, the number of days the purchased drugs may cover, and the number of days past a refill date.

In the example first entry 1003 of the list, its prescription number is 123456789012, the medication name is Cholestyramine, 250 mg tabs, the prescription was filled at a retail pharmacy store, the prescription was filled on Nov. 31, 2000, the supply would last 60 days, and the number of days past a refill date is 30 days.

The duration of time to store the medication history is, for example, 12 months for both mail and retail options, after which information maybe expunged.

The Days Late for Refill (Days past refill date) calculation is expressed as, for example:

| Current/Most Recent Date of Service | − | Date of Service from previous fill | − | Days of supply previous fill | = | Days late for refill |
|---|---|---|---|---|---|---|
| Jul. 17, 1998 | − | Apr. 15, 1998 | − | 90 | = | 3 |

The calculation determines the number of days resulting from the last refill date subtracted from the last date of service. If this number is greater than the number of days of supply of the last refill, then the difference indicates how many days past due that the medication may not be available to the patient. If the numbers are equal, the patient is due to refill today and a "0" is displayed. If the result of the calculation is less than the number of days of supply, then the display would show "N/A" as the patient is not late in refilling their prescription. If no prior fill is available, an "N/A" is displayed. In the event there is no history to report on the patient selected, alternate text (e.g., "No History To Be Reported") will be displayed instead of a blank table. However, in the event that a data element is missing, a blank cell will be displayed.

In some example embodiments, the login process, discussed in connection with "Login" page 303 of FIG. 3, can be achieved by the patient entering his/her name and a prescription number, an example of which is illustrated in FIG. 10.

The "Patient Requests" option illustrated in FIG. 9, when selected, causes a "Patient Specific Message" page to be displayed, an example of which is illustrated in FIG. 11. In the "Patient Requests" page, the patient is allowed to make selections regarding whether or not to renew the prescribed medication and whether or not to receive the medication via a mail prescription by a mail option.

The "Benefit information" option illustrated FIG. 9, when selected, causes a "Benefits" page to be displayed. The "Benefits" page, an example of which is illustrated in FIG. 12, displays copayment information. More specifically, FIG. 12 displays copay information when generic/brand name medication is to be purchased and when home delivery/retail pharmacy option is used.

The "Formulary" option illustrated FIG. 9, when selected, causes a "Formulary" page to be displayed. The medication "Formulary" page, an example of which is illustrated in FIG. 13, displays a number of commonly prescribed medications preferred by the medical/pharmaceutical care insurance carriers of the patient.

In particular, in some example embodiments of the present invention, as the patient enters the Web site, a formulary match process can optionally occur before the "Formulary" page is displayed to the member. The formulary match process includes the following steps: First, an indicator is checked to determine if the patient's health plan allows to display the formulary online. Second, a formulary ID of the patient is identified. The formulary ID is a number that is consistent across all claims submission types and match the appropriate formulary. The various Formulary pages, identifiable by the ID, can optionally be stored for each type of formulary with the expectation that updates can be provided on a regular basis, e.g., a quarterly basis. Next, the matched formulary is displayed. If no formulary matches, no formulary is displayed. In another example embodiment, a computer can be configured to allow the formulary to be created when needed by referencing a rules database that contains all the rules required to create such formularies. Then the formulary is displayed to the patient.

This Web page results in an accurate, up to date formulary. This information can help the patient to make the most of his/her benefits, while giving the physician information to help to prepare a correct prescription. The formulary also reduces the chance of incorrectly issuing prescriptions. (For example, an incorrect prescription includes drugs not preferred by the insurance carriers.)

The present invention advantageously provides a doctor kit that comprises a set of printed or electronic material that contains the patient specific information, for example, any combination of the medication history, patient requests, benefit information, formulary, prescription fax form and information and the like. The doctor kit provides the patient with a tool that he/she can use to assist the physician in making critical therapy decisions. Benefit information and medication history stored within the doctor kit can reflect the same information already accessible on the site under the "Benefits" page, FIG. 12, and the "Medication History" page, FIG. 10, respectively. It allows the patient to be more proactive and informed when reviewing their medication therapy with his/her physician. It also allows the patient to seek self-help. The kit can optionally include a fax prescription form described below in connection with FIG. 15.

The following is an example print of the doctor kit:

A "Patient Name" field 1402 includes the patient's first and last name.

A "Form Content" filed 1403 includes the format in which the content will be generated dynamically and merged with the data elements.

An "As of" Date 1404 includes the current date (format mm/dd/yy) representing the date the form was printed.

A "Member Id" field 1405 includes the identification number of the member entered at the registration stage.

A "Date of Birth" field 1406 includes patient's date of birth (format mm/dd/yy).

A "Group #" field 1407 includes the group health insurance ID associated with the member and prescription entered at the time of registration.

A "Key Image" field 1408 illustrates symbols representing whether the prescription was filled at a retail pharmacy or by a mail pharmacy.

A "Prescription Number/Medication Name/Strength (Mail/Retail)" field 1409 includes the medication name and strength. There may be multiple occurrences of the same medication here since the form will display prescription activity from the last 12 months. This information will be displayed in medication name and date of order dispensed (e.g., the date of the order).

A "Rx filled at" field 1410 includes a symbol representing whether the prescription was filled at a retail pharmacy or by a mail pharmacy.

A "Date filled" field 1411 includes a value representing the date the prescription was dispensed.

A "Quantity" field 1412 includes a value representing the total number of pills.

A "Days Supply" field 1413 includes a value representing the total number of days.

A "Days past refill date" field 1414 includes a computed value determined by subtracting the days supply of the previous fill from the difference of the most recent date of service and the date of service from the previous fill. The date from the previous fill will be used if available.

A "Drug Name—New Prescription" field 1415 provides information on those prescriptions that are currently "in process/open" that the patient has requested to renew.

A "Drug Name—Home Delivery" field 1416 provides information on those prescriptions that are currently "in process/open" that the patient has requested to fill by mail.

A "Type of Service" field 1417 represents the type of coverage that is currently available to the patient.

A "Maximum Days Supply" field 1418 shows information based on client plan specifics/definitions, this value represents the total number of days allowed to be dispensed by either mail or retail.

A "Generic Co-payment" field 1419 represents the dollar amount to be paid by the member when a generic medication is dispensed by either mail or retail.

A "Brand Co-payment" field 1420 represents the dollar amount to be paid by the member when a brand name medication is dispensed by either mail or retail.

The patient can view these segments one at a time or choose to print the entire kit. If printing is selected, all sections are to be generated and formatted to print correctly for the patient. It should be noted that the patient can also be given an option to print any subset or combination of the above described segments. For instance, the patient can choose to: (a) print his/her prescription history, (b) the prescription history plus benefit/coverage, or (c) allergies but not the prescription history. It should also be noted that the patient can be given an option to self enter known allergies, medical conditions and/or currently taking drugs (including over-the-counter drugs).

Example browsers to run the Doctor Kit include Netscape™, America Online™ with Microsoft IE™, and WebTv™. Furthermore, in at least some example embodiments of the present invention, when the patient prints their doctor kit, all appropriate information of the kit can be printed in one step. In these example embodiments, the Web site may be configured to support 5.0 & higher or Netscape 4.75 and higher, etc.

In one example embodiment, when the patient decides to print the doctor kit, he/she would click on the "Print the Kit" button found in the upper right-hand corner in FIGS. 10-14. When the print button is selected, a hidden frame in the page is populated with the five segments, or any combination thereof, of the doctor kit. During the loading of the hidden frame, a message is to be presented to the patient informing them that Doctor Kit is formatting. Once the frame is populated, the printout is to be sent to a printer. The hidden frame is to be populated with the entire Doctor Kit. The inclusion of the prescription history, patient specific messages, benefit information, formulary, and prescription fax form sections can be dependent on benefit type, eligibility status and formulary file match results. Alternately, the patient may download this report to the physicians' computer and/or mobile device or to their own device (e.g., PDA, disk, key card, storage media, etc.).

The above-described example Web pages advantageously deliver the patient-specific information at and around the time the physician issues a prescription, to thereby ensure that the correct prescription is written for the patient. The benefits of providing the patient information to the physician include: improved quality of patient care; improved formulary compliance; greater control over pharmacy costs; appropriate mail usage; reduced costs from prescribing errors, adverse drug reactions and poor patient compliance; and improved system for doctor-patient-pharmacy interactions.

The present invention also utilizes the "patient-influence" on the physician, since the physician is more likely to consider this information if it is provided directly by the patient. In addition, patient consent is required to release the information to the doctor, which is implicit when the patient provides the information directly to the doctor.

The Prescription Fax Form page, an example of which is illustrated in FIG. 15, is a printable page for faxing an issued prescription to a pharmacy (e.g., a mail order prescription service pharmacy.

Figure 16:
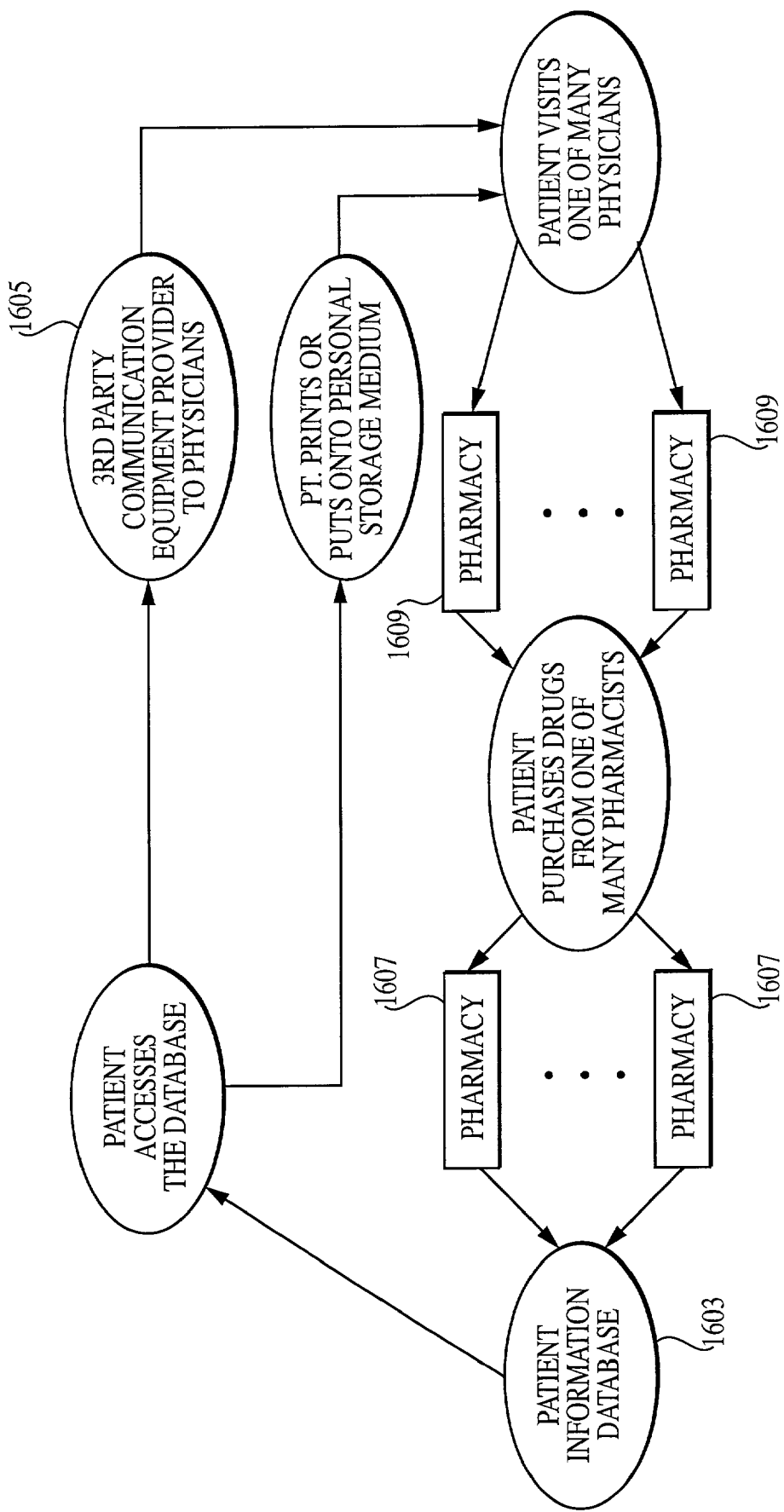
FIG. 16 is a flow chart illustrating various components in example embodiments of the present invention.

Various example computer components and methodologies of exemplary embodiments of the present invention are described below by referencing FIGS. 16-18. In particular, FIG. 16 illustrates various components of some example embodiments of the present invention, which include a patient information database 1603 and optional third party communication equipment 1605.

The patient information database 1603 is configured to store, sort, search and/or retrieve prescription information, and other information, examples of which have been described above in connection with FIGS. 4-13. Although the above-described examples in connections with FIGS. 4-13 show information relating to only one patient, the patient information database 1603 is configured to store, sort, search and/or retrieve prescription information, and other information, for many patients (e.g., up to or more than tens of millions of patients). In the patient information database, a database interface software package is configured to allow a patient to search/retrieve information only pertaining to him/her and his/her family members who have been registered as such. The database can be any commercially available (e.g., Sybase) or custom built systems.

The patient information database 1603 can be configured to store the prescription information, and other information, for an indefinite period of time. In an example alternative embodiment, the patient information database is optionally configured to store the prescription information, and other information, only for a predetermined length of time (e.g., 12 months).

The patient information database can receive and store prescription information of patients from any number of pharmacy stores 1607. The pharmacy store can be a local drug store (e.g., CVS, Walgreen, etc.) or can be a mail order prescription, PBM fulfillment company (e.g., Merck-Medco Managed Care, LLC). Each time the patient contacts any of the pharmacy stores 1607 (e.g., to fill a prescription or for a refill), the pharmacy store forwards relevant information to the patient information database 1603 to be stored (e.g., names and amount of drugs prescribed, names and amount of drugs purchased, etc.), via, for examples, a secured communication link over the Internet.

In some embodiments of the present invention, the patient is allowed to visit a pharmacy store that uses a second database different from the patient information database 1603. In such embodiments, the patient is given an option to transfer the data stored in the secondary database to the patient information database 1603. For example, in the My Prescriptions Web page, an option can be provided to transfer the data from the secondary database. (It should be noted that the present invention allows more than one secondary database.) When the patient selects the option to transfer the data from the secondary database, an interface is created between the secondary database and the patient information database 1603. Example steps of the interface may include matching patient's name and/or an identification number, e.g., the insurance member number, and then formatting the data stored in the secondary database so that the formatted data can be transferred and stored into the patient information database 1603. The interface can also be configured to transfer data between databases as known in the art. The interface may be created when the data transfer is performed or can be prearranged and created before the data transfer is performed.

In some example embodiments of the present invention, the patient is not limited to visiting only one physician. The patient can visit any number of physician 1609, whether or not the physician's visit is covered by the patient's health care insurance carrier. The patient may visit any physician because information relating to any prescription written by any physician is stored in the patient information database 1605. This allows the patient to print a complete prescription history, no matter how many different physicians have been visited by the patient. It should be noted that one physician cannot access prescription information relating to prescriptions written by other physicians without that patient's consent.

In particular, stored information in the patient information database is protected for privacy. More specifically, the database is configured such that no other person can access the stored information other than the patient or other family members, if they have been registered as such. In this way, no pharmacy or physician has access to the information stored in the patient information database without a proper authorization by the patient.

The patient may print the patient's specific information by using the Doctor Kit as discussed above. In an alternative embodiment, the patient may forward the patient specific information to the physician via the third party communication equipment 1605. It should be noted that whether prescription information is forwarded to the physician electronically, by printing and presenting the printed material to the physician, or forwarded using the third party communication equipment, the process is advantageously initiated or directed by the patient. In other words, the patient, either implicitly or explicitly, authorizes release of the prescription data to the physician.

Figure 17:
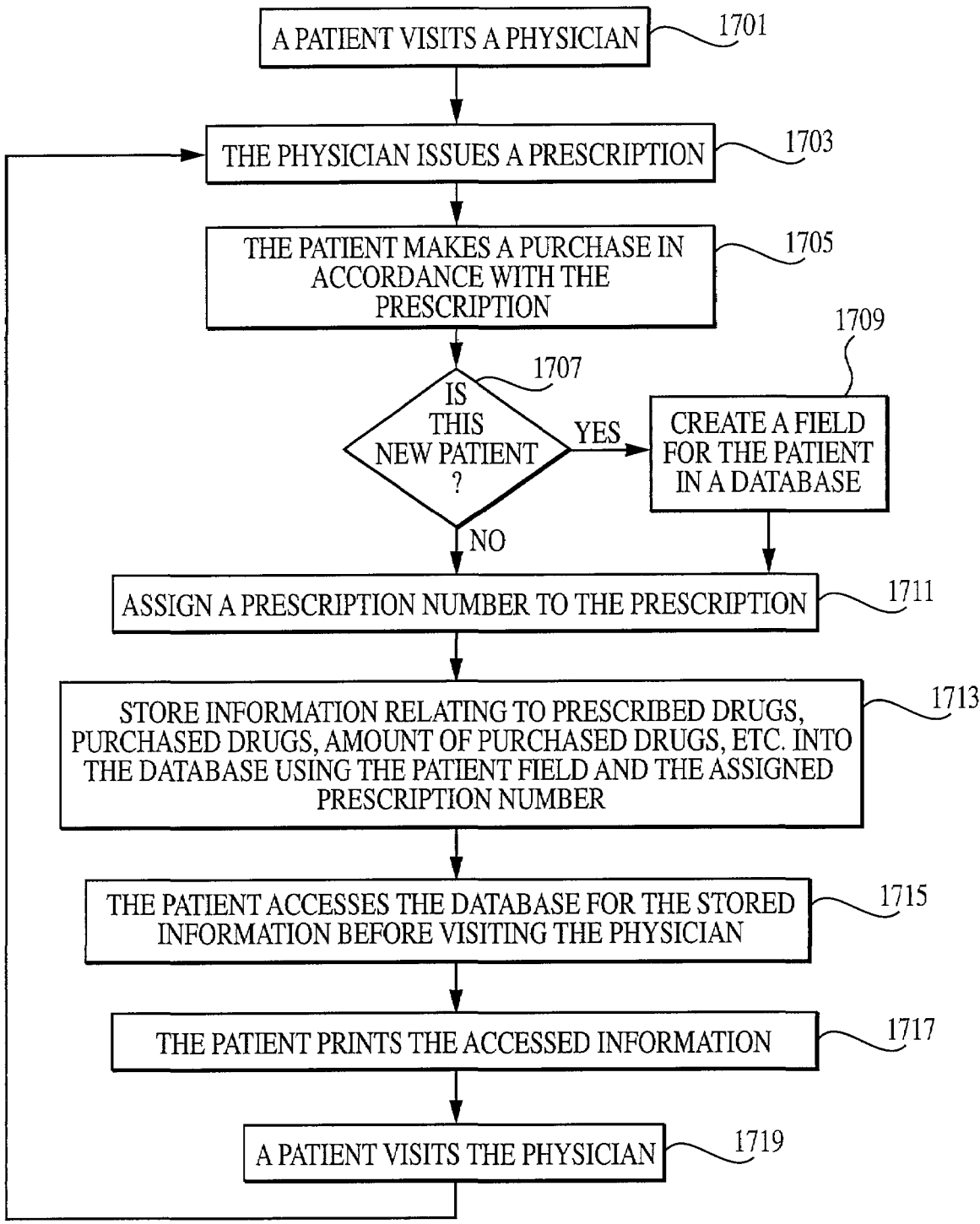
FIG. 17 is a flow chart illustrating the steps relating to the components shown in FIG. 16.

FIG. 17 illustrates example steps carried out by some example embodiments of the present invention. First, a patient visits a physician with or without the patient specific information (step 1701). The physician issues a prescription to treat any ailment the patient may possess (step 1703). The patient purchases a drug(s) in accordance with the prescription at a pharmacy store, either a local pharmacy store or a mail delivery company (step 1705). When the purchase is made, the pharmacy reports the purchase information to a computer that interfaces with the patient information database. The patient information database, more specifically, the interface computer, determines whether or not the patient is a new patient. If the patient is a new patient, the interface computer, creates a field in the patient information database to store information related to the patient (step 1709). If the patient is not a new patient, then the previously created field is located. The information received from the pharmacy is then stored in the field.

Information relating to each purchase is stored in the database by being associated with a reference number (e.g., a prescription number) (step 1711). The received information relating to prescribed drugs, purchased drugs, amount of purchased drugs, etc., is stored into the database using the patient field and the assigned prescription number (step 1713). Later, when the patient intends to visit one of many physicians, the patient can access the database for the stored information before visiting the physician (step 1715), as described above in connection with the example Web site illustrated in FIGS. 4-14. The accessed information is printed (or electronically communicated to the physician) by the patient (step 1717). The patient then visits the physician, optionally repeating the steps (step 1719).

Figure 18:
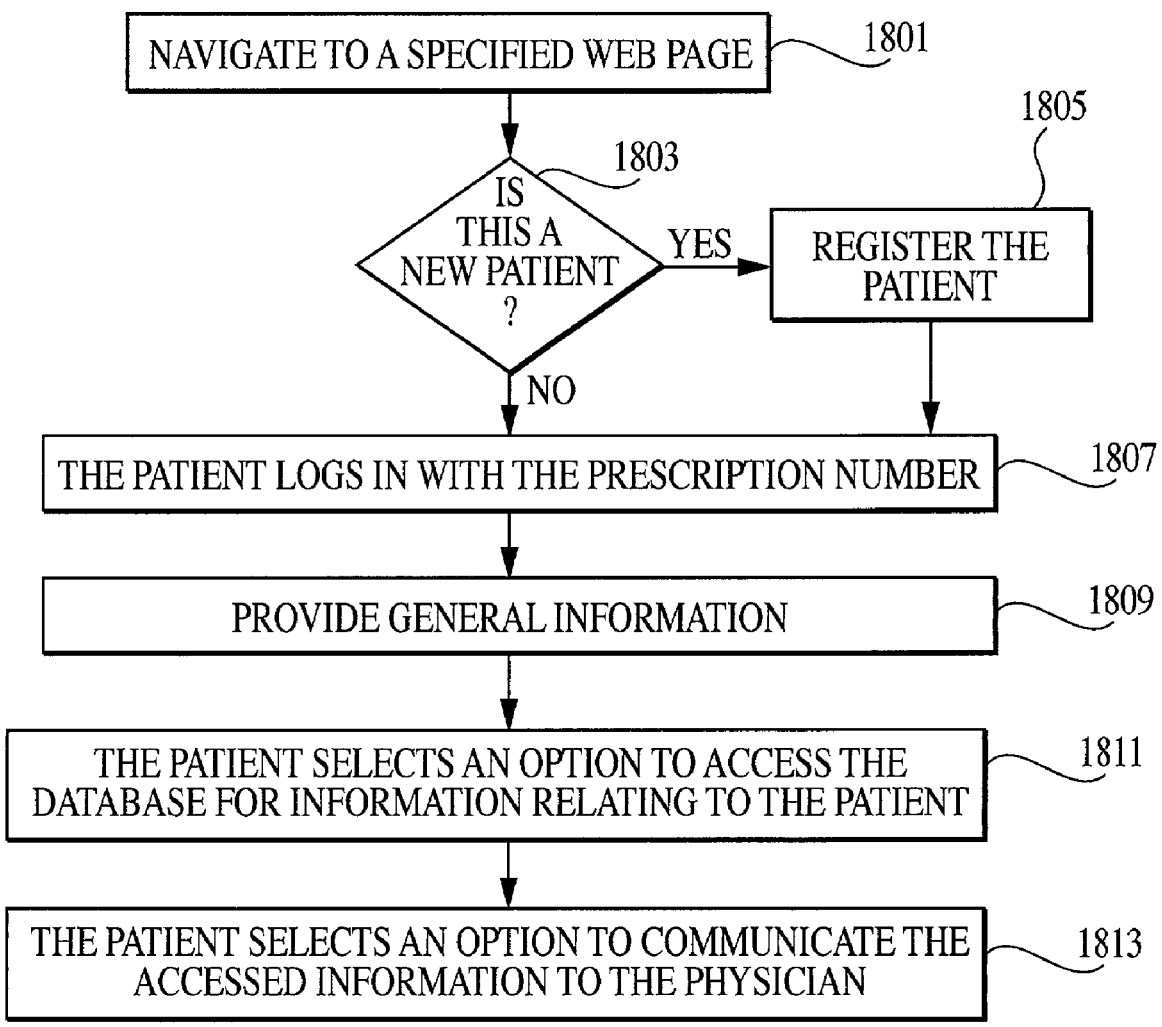
FIG. 18 is a flow chart illustrating the steps in accessing an example database by a patient.

FIG. 18 illustrates example steps in accessing the patient database by the patient. The patient first navigates to the Web site (step 1801). If the patient is a new patient, then the patient is required to register for the Web site (steps 1803 and 1805). If the patient is not a new patient, he/she may log in with a prescription number (step 1807). As shown above in FIG. 4, general information is then provided (step 1809). Subsequently, the patient selects an option to access the database for information relating to the patient (step 1811). The patient then selects an option (either print and present or electronic communication) to communicate the accessed information to the physician (step 1813).

Figure 19:
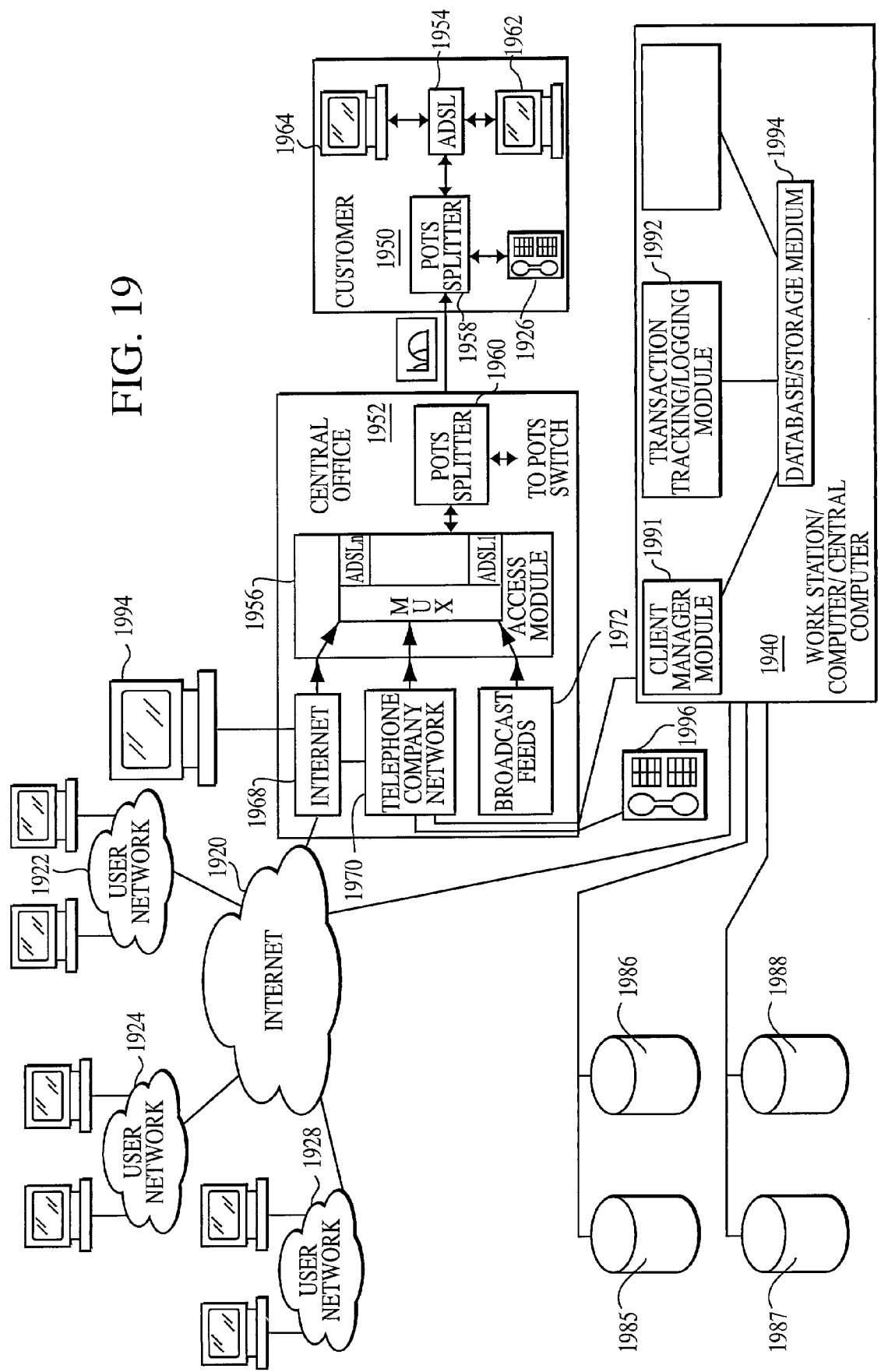
FIG. 19 is a block diagram representation of an example embodiment of computer network(s) implementing embodiments of the present invention.

FIG. 19 is an illustration of the architecture of the combined Internet, POTS (plain, old, telephone service), and ADSL (asymmetric, digital, subscriber line) for use in accordance with the principles of the present invention (e.g., accessing the Web site for various Web pages illustrated in FIGS. 4-13). Furthermore, it is to be understood that the use of the Internet, ADSL, and POTS are for exemplary reasons only and that any suitable communications network may be substituted without departing from the principles of the present invention. This particular example is briefly discussed below.

In FIG. 19, to preserve POTS and to prevent a fault in the ADSL equipment 1954, 1956 from compromising analog voice traffic 1926, 1996 the voice part of the spectrum (the lowest 4 kHz) is separated from the rest by a passive filter, called a POTS splitter 1958, 1960. The rest of the available bandwidth—from about 10 kHz to 1 MHz—carries data at rates up to 6 bits per second for every hertz of bandwidth from data equipment 1962, 1964, and 1994. The ADSL equipment 1956 then has access to a number of destinations including significantly the Internet 1920 or other data communications networks, and other destinations 1970, 1972.

To exploit the higher frequencies, ADSL makes use of advanced modulation techniques, of which the best known is the discrete multitone (DMT) technology. As its name implies, ADSL transmits data asymmetrically—at different rates upstream toward the central office 1952 and downstream toward the subscriber 1950.

Cable television services are providing analogous Internet service to PC users over their TV cable systems by means of special cable modems. Such modems are capable of transmitting up to 30 Mb/s over hybrid fiber/coax system, which use fiber to bring signals to a neighborhood and coax to distribute it to individual subscribers.

Cable modems come in many forms. Most create a downstream data stream out of one of the 6-MHz TV channels that occupy spectrum above 50 MHz (and more likely 550 MHz) and carve an upstream channel out of the 5-50-MHz band, which is currently unused. Using 64-state quadrature amplitude modulation (64 QAM), a downstream channel can realistically transmit about 30 Mb/s (the oft-quoted lower speed of 10 Mb/s refers to PC rates associated with Ethernet connections). Upstream rates differ considerably from vendor to vendor, but good hybrid fiber/coax systems can deliver upstream speeds of a few megabits per second. Thus, like ADSL, cable modems transmit much more information downstream than upstream. Then Internet architecture 1920 and ADSL architecture 1954, 1956 may also be combined with, for example, user networks 1922, 1924, and 1928.

In accordance with the principles of the present invention, in one example, a main computing server implementing the process of the invention may be located on one or more computing nodes or terminals (e.g., on user networks 1922, 1924, and 1928 or system 1940). Then, various users may interface with the main server via, for instance, the ADSL equipment discussed above, and access the information and processes of the present invention from remotely located PCs. As illustrated in this embodiment, users may access, use or interact with the computer assisted program in computer system 1940 via various access methods. Databases 1985, 1986, 1987, 1988, and 1940 are accessible via, for example computer system 1940 and may be used in conjunction with client manager module 1991, tracking module 1992, for the various functions described above.

Figure 20:
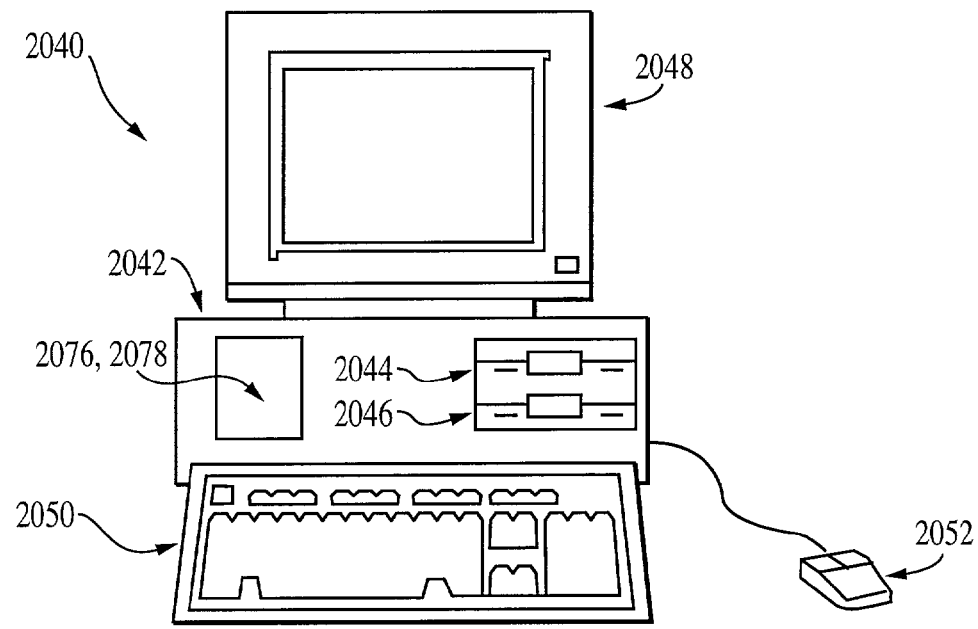
FIG. 20 illustrates a computer that can be used in implementing embodiments of the present invention.

Viewed externally in FIG. 20, a computer system designated by reference numeral 2040 has a computer 2042 having disk drives 2044 and 2046. Disk drive indications 2044 and 2046 are merely symbolic of a number of disk drives which might be accommodated by the computer system. Typically, these would include a floppy disk drive 2044, a hard disk drive (not shown externally) and a CD ROM indicated by slot 2046. The number and type of drives vary, typically with different computer configurations. Disk drives 2044 and 2046 are in fact optional, and for space considerations, are easily omitted from the computer system used in conjunction with the production process/apparatus described herein.

The computer system also has an optional display upon which information screens may be displayed. In some situations, a keyboard 2050 and a mouse 2052 are provided as input devices through which a user's actions may be inputted, thus allowing input to interface with the central processing unit 2042. Then again, for enhanced portability, the keyboard 2050 is either a limited function keyboard or omitted in its entirety. In addition, mouse 2052 optionally is a touch pad control device, or a track ball device, or even omitted in its entirety as well, and similarly may be used to input a user's selections. In addition, the computer system also optionally includes at least one infrared transmitter and/or infrared received for either transmitting and/or receiving infrared signals, as described below.

Figure 21:
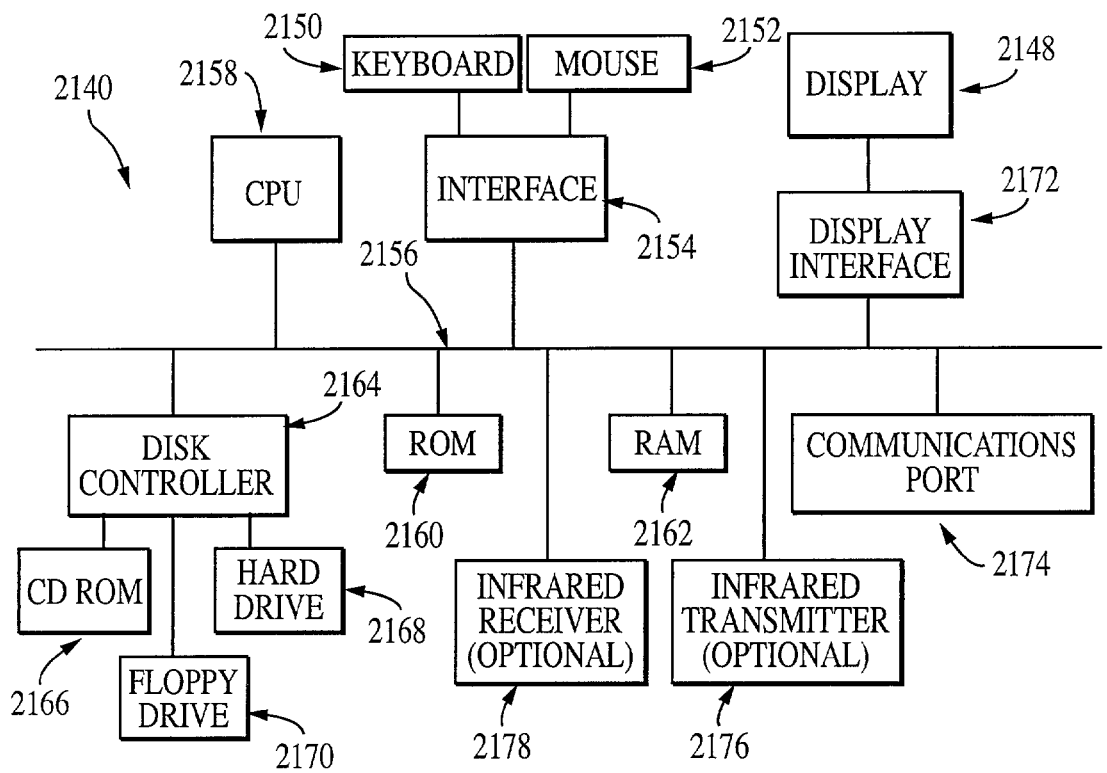
FIG. 21 is a block diagram of internal hardware of the example computer shown in FIG. 20.

FIG. 21 illustrates a block diagram of one example of the internal hardware configured to perform a server function for the Web pages described above. A bus 2156 serves as the main information highway interconnecting various components therein. CPU 2158 is the central processing unit of the internal hardware 2140, performing calculations and logic operations required to execute the control/operation processes of the present invention as well as other programs. Read only memory (ROM) 2160 and random access memory (RAM) 2162 constitute the main memory of the internal hardware 2140. Disk controller 2164 interfaces one or more disk drives to the system bus 2156. These disk drives are, for example, floppy disk drives 2170, or CD ROM or DVD (digital video disks) drives 2166, or internal or external hard drives 2168. These various disk drives and disk controllers are optional devices.

A display interface 2172 interfaces display 2148 and permits information from the bus 2156 to be displayed on display 2148. Display 2148 may be used in displaying various Web pages. Communications with external devices such as the other components of the system described above, occur utilizing, for example, communication port 2174. Optical fibers and/or electrical cables and/or conductors and/or optical communication (e.g., infrared, and the like) and/or wireless communication (e.g., radio frequency (RF), and the like) can be used as the transport medium between the external devices and communication port 2174. Peripheral interface 2154 interfaces the keyboard 2150 and mouse 2152, permitting input data to be transmitted to bus 2156. In addition to these components, the internal hardware 2140 also optionally include an infrared transmitter and/or infrared receiver. Infrared transmitters are optionally utilized when the computer system is used in conjunction with one or more of the processing components/stations/modules that transmits/receives data via infrared signal transmission. Instead of utilizing an infrared transmitter or infrared receiver, the computer system may also optionally use a low power radio transmitter 2180 and/or a low power radio receiver 2182. The low power radio transmitter transmits the signal for reception by components of the production process, and receives signals from the components via the low power radio receiver. The low power radio transmitter and/or receiver are standard devices in industry.

Although the server in FIG. 21 is illustrated having a single processor, a single hard disk drive and a single local memory, the analyzer is optionally suitably equipped with any multitude or combination of processors or storage devices. For example, the computer may be replaced by, or combined with, any suitable processing system operative in accordance with the principles of embodiments of the present invention, including sophisticated calculators, and hand-held, laptop/notebook, mini, mainframe and super computers, as well as processing system network combinations of the same.

Figure 22:
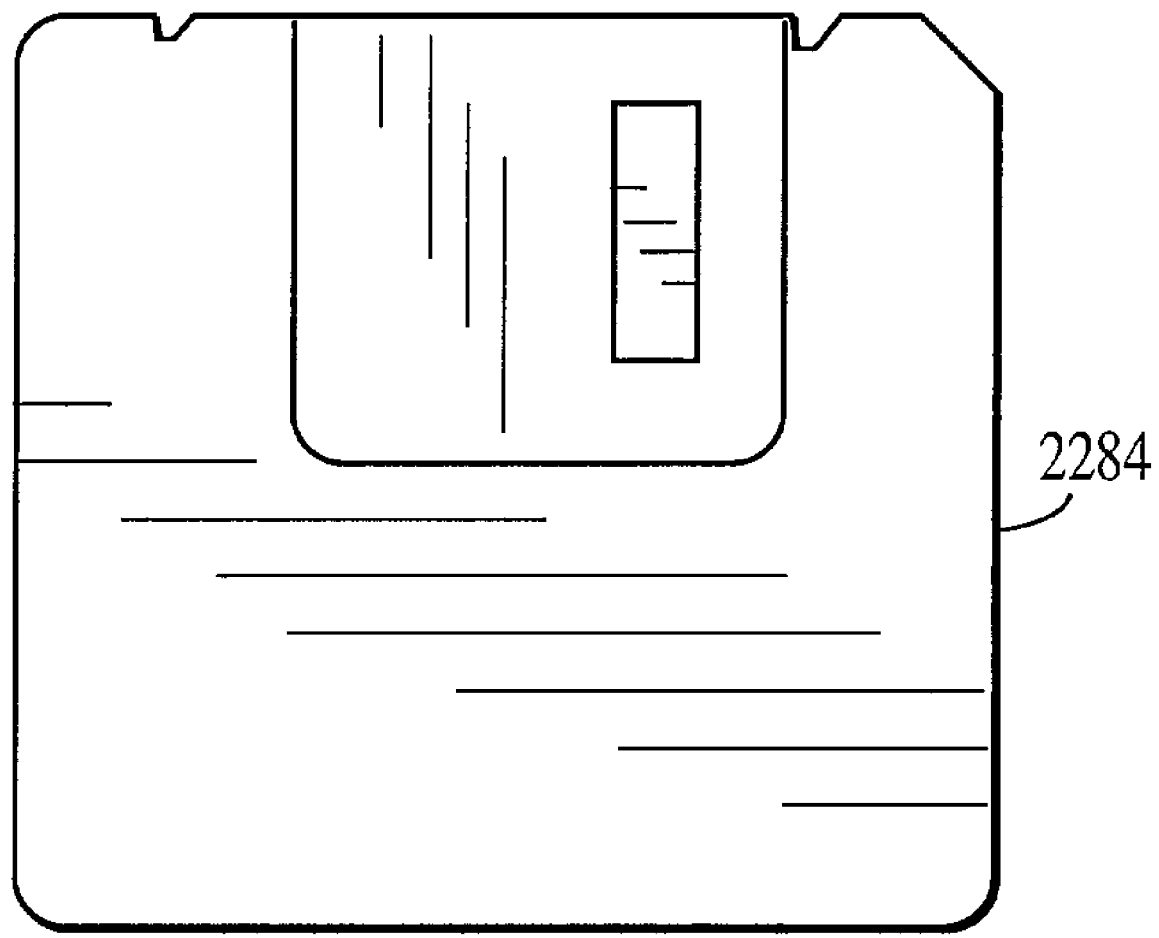
FIG. 22 illustrates one example of a memory medium which may be used for storing computer programs of embodiments of the present invention.

FIG. 22 is an illustration of an example computer readable memory medium 2284 utilizable for storing computer readable code or instructions. As one example, medium 2284 may be used with disk drives illustrated in FIG. 21. Typically, memory media such as floppy disks, or a CD ROM, or a digital video disk will contain, for example, a multi-byte locale for a single byte language and the program information for controlling the modeler to enable the computer to perform the functions described herein. Alternatively, ROM 2160 and/or RAM 2162 illustrated in FIG. 21 can also be used to store the program information that is used to instruct the central processing unit 2158 to perform the operations associated with various automated processes of the present invention. Other examples of suitable computer readable media for storing information include magnetic, electronic, or optical (including holographic) storage, some combination thereof, etc.

In general, it should be emphasized that the various components of embodiments of the present invention can be implemented in hardware, software or a combination thereof. In such embodiments, the various components and steps would be implemented in hardware and/or software to perform the functions of embodiments of the present invention. Any presently available or future developed computer software language and/or hardware components can be employed in such embodiments of the present invention. For example, at least some of the functionality mentioned above could be implemented using Visual Basic, C, C++, or any assembly language appropriate in view of the processor(s) being used. It could also be written in an interpretive environment such as Java and transported to multiple destinations to various users.

The many features and advantages of embodiments of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A computer-assisted method of providing, to a health care provider, information relating to a patient, said method comprising the steps of:
   (a) collecting a prescription history that includes information relating to one or more prescriptions issued to the patient, a non-prescription purchase history, and a prescription purchase history that includes information relating to one or more prescription purchases made by the patient in accordance with the one or more prescriptions, said collecting step (a) further comprising:
      (1) collecting the prescription history and prescription purchase history information when the one or more prescriptions are issued by different health care providers; and
      (2) collecting the prescription history and prescription purchase history information when drugs prescribed in the one or more prescriptions are purchased from different pharmacists including, when information exists, a retail pharmacy, pharmaceutical benefits management company and mail delivery pharmacy;
   (b) storing the prescription history, non-prescription purchase history, and prescription purchase history information of the patient into a database when at least one of the one or more prescriptions are issued by at least one of different health care providers and different pharmacists;
   (c) determining whether a drug formulary exists associated with a pharmacy insurance carrier of the patient;
   (d) generating, when it is determined that the drug formulary is not in existence, the drug formulary associated with the pharmacy insurance carrier of the patient by referencing a rules database, the drug formulary matches a formulary identification number of the patient, wherein the formulary identification number is consistent with different insurance carriers of the patient and specific to a formulary;
   (e) accessing the information stored in the database for the prescription history, non prescription purchase history, and prescription purchase history of the patient, wherein access will be granted only for the patient or a representative of the patient, under the direction of the patient or the representative, and under the authorization by the patient or the representative;
   (f) retrieving the information relating to prescription history, non-prescription purchase history, and prescription purchase history by the patient or the representative; and
   (g) at least one of printing and displaying, by the patient or the representative, the information retrieved relating to the prescription history, non-prescription purchase history, prescription purchase history, and information associated with said formulary, wherein said formulary is associated with the patient's insurance company for the health care provider in order to assist the health care provider in providing health care to the patient to prescribe for the patient the one or more prescriptions.

2. The method of claim 1, wherein step (f) of printing by the patient comprises:
   sending, by the patient, to the health care provider an electronic message that contains the retrieved prescription history, non-prescription purchase history, and prescription purchase history.

3. The method of claim 2, wherein the electronic message is delivered to a platform that is capable of receiving an electronic message.

4. The method, wherein step (b) of claim 1, further comprising the step of:
   storing to the database information relating to pharmacy benefits for the patient and information relating to a drug formulary preferred by a pharmacy insurance carrier of the patient.

5. The method of claim 4 further comprising the steps of:
   accessing, by the patient or the representative, the database for the stored information relating to pharmacy benefits for the patient and the preferred drug formulary; and
   retrieving the information relating to pharmacy benefits for the patient and the preferred drug formulary.

6. The method of claim 5 further comprising the steps of:
   printing the information relating to pharmacy benefits for the patient and the preferred drug formulary and information relating to the retrieved prescription history, non-prescription purchase history, and prescription purchase history; and
   presenting, by the patient or the representative, the printed information to the health care provider.

7. The method of claim 6, wherein the printing step comprises the steps of:
   combining the information relating to pharmacy benefits for the patient and the preferred drug formulary and information relating to the retrieved prescription history, non-prescription purchase history, and prescription purchase history; and
   formatting the combined information into a form presentable to the health care provider.

8. The method according to claim 7, wherein the health care provider is at least one of a physician, osteopath and pharmacist.

9. The method of claim 1, wherein the representative of the patient is at least one of patient's parent and patient's guardian.

10. The method of claim 1, wherein said step (b) of determining whether a drug formulary is in existence further comprises the steps of:
   (a) compiling a database, wherein the generated formulary is stored;
   (b) associating said formulary using said formulary ID;
   (c) retrieving said formulary associated with said formulary ID; and
   (d) displaying said formulary that are determined to match said formulary ID.

11. The method of claim 10 further comprising the determination whether a patient's insurance plan allows said formulary to be displayed online and the determination of a formulary id specific to the patient.

12. A method of providing, to a health care provider, printed or displayed information relating to a patient's health care, said method comprising the steps of:

(a) collecting a prescription history that includes information relating to one or more prescriptions issued to the patient, a non-prescription purchase history comprising at least one of herbal medicines, naturopathic medicines, and over-the-counter medicine, and a prescription purchase history that includes information relating to one or more prescription purchases made by the patient in accordance with the one or more prescriptions, said collecting step (a) further comprising:

(1) collecting the prescription history and prescription purchase history information when the one or more prescriptions are issued by different health care providers; and (2) collecting the prescription history and prescription purchase history information when drugs prescribed in the one or more prescriptions are purchased from different pharmacists including, when information exists, a retail pharmacy, pharmaceutical benefits management company and mail delivery pharmacy;

(b) determining whether a drug formulary exists associated with a pharmacy insurance carrier of the patient;

(c) generating, when it is determined that the drug formulary is not in existence, the drug formulary associated with the pharmacy insurance carrier of the patient by referencing a rules database, the drug formulary matches a formulary identification number of the patient, wherein the formulary identification number is consistent with different insurance carriers of the patient and specific to a formulary;

(d) storing the prescription history, non-prescription purchase history, and prescription purchase history information of the patient into a database when at least one of the one or more prescriptions are issued by at least one of different health care providers and different pharmacists;

(e) storing to the database information relating to pharmacy benefits for the patient and information relating to the drug formulary;

(f) accessing the database for the stored information, wherein access is granted only for the patient or a representative of the patient, under the direction of the patient or the representative, and under the authorization by the patient or the representative;

(g) retrieving the accessed information; and (h) at least one of printing and displaying, by the patient or the representative, the retrieved information and information associated with the formulary, wherein the formulary is associated with the patient's insurance company, for the health care provider in order to assist the health care provider in providing medical services to the patient wherein the health care information is suitable for assisting the health care provider to render health care at a point of care to prescribe for the patient the one or more prescriptions.

13. The method of claim 12, wherein step (g) of printing by the patient comprises:

sending, by the patient or the representative, to the health care provider an electronic message that contains the retrieved information.

14. The method of claim 13, wherein the electronic message is delivered to a platform that is capable of receiving an electronic message.

15. The method according to claim 12, wherein the health care provider is at least one of a physician, osteopath and pharmacist.

16. The method of claim 12, wherein the representative of the patient is at least one of patient's parent and patient's guardian.

17. A computer assisted system for providing, to a health care provider, printed or displayed information relating to a patient, said system comprising:

(a) means for collecting a prescription history that includes information relating to one or more prescriptions issued to the patient, a non-prescription purchase history comprising at least one of herbal medicines, naturopathic medicines, and over-the-counter medicine, and a prescription purchase history that includes information relating to one or more prescription purchases made by the patient in accordance with the one or more prescriptions, said means for collecting further comprising:

(1) means for collecting the prescription history and prescription purchase history information when the one or more prescriptions are issued by different health care providers; and (2) means for collecting the prescription history and prescription purchase history information when drugs prescribed in the one or more prescriptions are purchased from different pharmacists including, when information exists, a retail pharmacy, pharmaceutical benefits management company and mail delivery pharmacy;

(b) means for storing the prescription history, non-prescription purchase history, and prescription purchase history information of the patient into a database when at least one of the one or more prescriptions are issued by at least one of different health care providers and different pharmacists;

(c) means for determining whether a drug formulary exists associated with a pharmacy insurance carrier of the patient;

(d) means for generating, when it is determined that the drug formulary is not in existence, the drug formulary associated with the pharmacy insurance carrier of the patient by referencing a rules database, the drug formulary matches a formulary identification number of the patient, wherein the formulary identification number is consistent with different insurance carriers of the patient and specific to a formulary;

(e) means for accessing the database for the prescription history, non-prescription history, and prescription purchase history information of the patient, wherein access is granted only for the patient, under the direction of the patient and under the authorization by the patient;

(f) means for retrieving the prescription history and prescription purchase history; and (g) means for at least one of printing and displaying, for the patient, the retrieved prescription history, non-prescription purchase history, prescription purchase history and information associated with the formulary, wherein said formulary is associated with the patient's insurance company for the prescriber health care provider in order to assist the provider in providing medical services to the patient, to thereby allow the health care provider to compare one or more issued prescriptions, non-prescription purchase history, and the prescription purchase history and prescribe the one or more prescriptions.

18. The system of claim 17, wherein the means (f) for printing for the patient comprises:

means for sending, for the patient, to the health care provider an electronic message that contains the retrieved prescription history, non-prescription purchase history, and prescription purchase history.

19. The system of claim 18, wherein the electronic message is delivered to a platform that is capable of receiving an electronic message.

20. The system of claim 17 further comprising:
means for providing and storing to the database information relating to pharmacy benefits for the patient and information relating to a drug formulary preferred by a pharmacy insurance carrier of the patient, wherein the pharmacy benefits and drug formulary information are suitable for assisting the health care provider to provide medical treatment to the patient.

21. The system of claim 20 further comprising:
means for accessing, for the patient, the database for the stored information relating to pharmacy benefits for the patient and the preferred drug formulary; and
means for retrieving the information relating to pharmacy benefits for the patient and the preferred drug formulary.

22. The system of claim 21 further comprising:
means for printing the information relating to pharmacy benefits for the patient and the preferred drug formulary and information relating to the retrieved prescription history, non-prescription purchase history, and prescription purchase history, thereby allowing the patient to present the printed information to the health care provider.

23. The system of claim 22, wherein the printing means comprises:
means for combining the information relating to pharmacy benefits for the patient and the preferred drug formulary and information relating to the retrieved prescription history, non-prescription purchase history, and prescription purchase history; and
means for formatting the combined information into a form presentable to the health care provider.

24. The system of claim 17, wherein the health care provider is at least one of a physician, osteopath and pharmacist.

25. A system of providing, to a health care provider, printed or displayed information relating to a patient, said system comprising:
(a) means for collecting a prescription history that includes information relating to one or more prescriptions issued to the patient, a non-prescription purchase history comprising at least one of herbal medicines, naturopathic medicines, and over-the-counter medicine, and a prescription purchase history that includes information relating to one or more prescription purchases made by the patient in accordance with the one or more prescriptions and collecting pharmacy benefits and drug formulary preformed by pharmacy insurance carrier, said means for collecting further comprising:
(1) means for collecting the prescription history and prescription purchase history information when the one or more prescriptions are issued by different health care providers; and
(2) means for collecting the prescription history and prescription purchase history information when drugs prescribed in the one or more prescriptions are purchased from different pharmacists including, when information exists, a retail pharmacy, pharmaceutical benefits management company and mail delivery pharmacy;

(b) means for determining whether a drug formulary exists associated with a pharmacy insurance carrier of the patient;
(c) means for generating, when it is determined that the drug formulary is not in existence, the drug formulary associated with the pharmacy insurance carrier of the patient by referencing a rules database, the drug formulary matches a formulary identification number of the patient, wherein the formulary identification number is consistent with different insurance carriers of the patient and specific to a formulary;
(d) means for storing the prescription history, non-prescription purchase history, and prescription purchase history of the patient into a database and storing information relating to pharmacy benefits for the patient and information relating to a drug formulary preferred by a pharmacy insurance carrier of the patient when at least one of the one or more prescriptions are issued by at least one of different health care providers and different pharmacists, wherein the pharmacy includes at least one of a retail pharmacy, pharmaceutical benefits management company, and mail delivery pharmacy;
(e) means for storing to the database information relating to pharmacy benefits for the patient and information relating to the drug formulary;
(f) means for accessing the information stored in the database, wherein access is granted only for the patient under the direction of the patient, and under the authorization by the patient, the database for the stored information;
(g) means for retrieving the accessed information; and
(h) means for at least one of printing and displaying, by or on behalf of the patient, the retrieved information for the health care provider and information associated with the formulary in order to assist the provider in providing medical services to the patient to prescribe for the patient the one or more prescriptions.

26. The system of claim 25, wherein the means (g) for printing by the patient comprises:
means for sending, by or for the patient, to the provider an electronic message that contains the retrieved information.

27. The system of claim 26, wherein the electronic message is at least one of a PDA message, PC message, pager message, and fax message.

28. The system of 25 wherein the health care provider is at least one of a physician, osteopath and pharmacist.

29. A computer readable medium for storing instructions being executed by one or more computers, the instructions directing the one or more computers for providing, to a medical care provider, prescription and insurance information relating to a patient, the instructions comprising implementation of the steps of:
(a) determining whether a drug formulary exists associated with a pharmacy insurance carrier of the patient;
(b) generating, when it is determined that the drug formulary is not in existence, one or more prescription formularies preferred by a pharmacy insurance carrier of the patient by referencing a rules database, the one or more prescription formularies that match a formulary identification number of the patient, wherein the formulary identification number is consistent with different insurance carriers of the patient and specific to a formulary;
(c) collecting a prescription history that includes information relating to one or more prescriptions issued to the patient, a non-prescription purchase history, and a prescription purchase history that includes information relating to one or more prescription purchases made by the patient in accordance with the one or more prescription formularies and insurance coverage, said collecting further comprising:
- (1) collecting the prescription history and prescription purchase history information when the one or more prescriptions are issued by different health care providers; and
- (2) collecting the prescription history and prescription purchase history information when drugs prescribed in the one or more prescriptions are purchased from different pharmacists including, when information exists, a retail pharmacy, pharmaceutical benefits management company and mail delivery pharmacy;

(d) storing the prescription history, non-prescription purchase history, and prescription purchase history of the patient into a database and storing information relating to pharmacy benefits for the patient and information relating to a drug formulary preferred by a pharmacy insurance carrier of the patient when at least one of the one or more prescriptions are issued by at least one of different health care providers and different pharmacists, wherein the pharmacy includes at least one of a retail pharmacy, pharmaceutical benefits management company, and mail delivery pharmacy;

(e) accessing the database for the stored prescription history, non-prescription purchase history, and prescription history of the patient, wherein access is granted only for the patient, under the direction of the patient and under the authorization by the patient;

(f) retrieving the prescription history, non-prescription purchase history, and prescription purchase history; and (g) at least one of printing and displaying the retrieved prescription history, non-prescription purchase history, prescription purchase history, and information associated with the formulary to the medical care provider in order to assist the medical care provider in providing medical services to the patient, wherein the accessing step and the communicating step are initiated by the patient to prescribe for the patient the one or more prescriptions.

30. The method of claim 29, wherein the step (f) of printing by the patient comprises:
sending to the medical care provider an electronic message that contains the retrieved prescription history and prescription purchase history.

31. The medium of claim 30, wherein the electronic message is a PDA message.

32. The medium of claim 29 further comprising the step of:
storing to the database information relating to pharmacy benefits for the patient and information relating to a drug formulary preferred by a pharmacy insurance carrier of the patient.

33. The medium of claim 32 further comprising the steps of:
accessing the database for the stored information relating to pharmacy benefits for the patient and the preferred drug formulary; and
retrieving the information relating to pharmacy benefits for the patient and the preferred drug formulary, wherein the accessing step is initiated by the patient.

34. The medium of claim 33 further comprising the steps of:
printing the information relating to pharmacy benefits for the patient and the preferred drug formulary and information relating to the retrieved prescription history, non-prescription purchase history, and prescription purchase history, to thereby allow the patient to present the printed information to the medical care provider.

35. The medium of claim 34, wherein the printing step comprises the steps of:
combining the information relating to pharmacy benefits for the patient and the preferred drug formulary and information relating to the retrieved prescription history, non-prescription purchase history, and prescription purchase history; and
formatting the combined information into a form presentable to the medical care provider.

36. The medium of claim 29, wherein the medical care provider is at least one of a physician, osteopath and pharmacist.

37. A computer readable medium including instructions being executed by one or more computers, the instructions instructing the one or more computers for providing, to a physician, information relating to a patient, the instructions comprising implementation of the steps of:

(a) determining whether a drug formulary exists associated with a pharmacy insurance carrier of the patient;

(b) generating, when it is determined that the drug formulary is not in existence, formulary information that matches a formulary identification number of the patient by referencing a rules database, wherein the formulary identification number is consistent with different insurance carriers of the patient and specific to a formulary;

(c) collecting a prescription history that includes information relating to one or more prescriptions issued to the patient, a non-prescription purchase history, and a prescription purchase history that includes information relating to one or more purchases made by the patient in accordance with the one or more prescriptions, insurance coverage and the formulary information and information relating to at least one of past prescriptions issued to the patient by either the treating physician or other physicians, whether or not the prescribed drugs have been purchased by the patient, when the prescribed drugs were purchased, the quantity of prescribed drugs purchased, the number of days past from a refill date when a prescription has not been refilled, when one or more prescriptions are issued by different health care providers, and when or more prescriptions are purchased from different pharmacists including, when information exists, a retail pharmacy, pharmaceutical benefits management company and mail delivery pharmacy;

(d) storing the prescription history, non-prescription purchase history, and prescription purchase history of the patient into a database when at least one of the one or more prescriptions are issued by at least one of different health care providers and different pharmacists;

(e) accessing the information stored in the database, wherein access is granted for the patient, under the direction of the patient and under the authorization by the patient and further comprising allowing the patient to access information related to at least one of benefits, a prescription expense summary, and an account summary and allowing the patient to access stored information relating to family members of the patient and allowing the patient to access stored information relating to, at least one of, prescriptions filled by a mail prescription filler and prescriptions filled by a local pharmacy store;

(f) retrieving the accessed information;

(g) at least one of printing and displaying the retrieved information and information associated with the formulary for the physician in order to assist the physician in providing medical services to the patient, wherein the accessing step and the communicating step are initiated by the patient to prescribe for the patient the one or more prescriptions;

(h) collecting the prescription history and prescription purchase history when the one or more prescriptions are issued by different physician;

(i) collecting the prescription history and prescription purchase history information when drugs prescribed in the one or more prescriptions are purchased from different pharmacists wherein the different pharmacists include at least one pharmacy that delivers the one or more prescriptions via mail; and (j) collecting the prescription history and prescription purchase history when one or more drug prescribed in the one or more prescriptions are purchased from different pharmacists that use different database to store the collected information.

38. The method of claim 37, wherein the step (f) of printing by the patient comprises:
sending, by the patient, to the physician an electronic message that contains the retrieved information.

39. The medium of claim 38, wherein the electronic message is a PDA message.

40. The medium of claim 37, wherein the prescription information includes, at least one of:
a prescription number;
a prescribed drug name;
the name of the physician;
a number of remaining refills;
a date on which the prescription was received; and
a date on which the prescription was shipped.

41. The medium of claim 37, further comprising the steps of allowing the patient to perform at least one of:
locating a retail pharmacy;
requesting envelopes and forms for returning filled prescriptions;
printing a mail service form;
refilling or renewing a prescription;
requesting a new prescription;
starting with mail service; and
purchasing over-the-counter pharmaceutical and other products.

42. The medium of claim 37, wherein the step (f) of communicating by the patient comprises the steps of printing, by the patient, the retrieved information and additional information related to at least one of:
one or more requests made by the patient;
a formulary of drugs; and
a form to fax a prescription, to thereby allow the patient to present the printed information to the physician.

43. The medium of claim 37,
wherein the step (f) of communicating by the patient comprises the steps of printing, by the patient, the retrieved information, to thereby allow the patient to present the printed information to the physician; and
wherein the patient is allowed to collect information relating to self-help using the printed information.

44. The medium of claim 37, wherein the step (f) of printing by the patient comprises the steps of printing, by the patient, the retrieved information and additional information relating to at least one of:
days past refill date;
information on one or more prescriptions that are currently in process or open that the patient has requested to renew;
information on one or more prescriptions that are currently in process or open that the patient has requested to fill by mail;
a type of coverage that is currently available to the patient;
a total number of days of drug supplies allowed to be dispensed to the patient;
a dollar amount to be paid by the patient when a generic medication is dispensed; and
a dollar amount to be paid by the patient when a brand name medication is dispensed, to thereby allow the patient to present the printed information to the physician.

45. The medium of claim 37, wherein the step (f) of printing by the patient comprises the step of:
creating a patient field in the database when the patient is a new patient.

46. The medium of claim 37, wherein the health care provider is at least one of a physician, osteopath and pharmacist.

47. A computer-assisted method of providing, to a physician, information relating to a patient, said method comprising the steps of:

(a) collecting a prescription history that includes information relating to one or more prescriptions issued to the patient, a non-prescription purchase history comprising at least one of herbal medicines, naturopathic medicines, and over-the-counter medicine, and a prescription purchase history that includes information relating to one or more prescription purchases made by the patient in accordance with the one or more prescriptions and information relating to at least one of past prescriptions issued to the patient by either the treating physician or other physicians, whether or not the prescribed drugs have been purchased by the patient, when the prescribed drugs were purchased, the quantity of prescribed drugs purchased, the number of days past from a refill date when a prescription has not been refilled, when one or more prescriptions are issued by different health care providers, and when or more prescriptions are purchased from different pharmacists including, when information exists, a retail pharmacy, pharmaceutical benefits management company and mail delivery pharmacy;

(b) storing the prescription history, non-prescription purchase history, and prescription purchase history information of the patient into a database and storing information relating to pharmacy benefits for the patient and information relating to a drug formulary preferred by a pharmacy insurance carrier of the patient when at least one of the one or more prescriptions are issued by at least one of different health care providers and different pharmacists, wherein the pharmacy includes at least one of a retail pharmacy, pharmaceutical benefits management company, and mail delivery pharmacy;

(c) determining whether a drug formulary exists associated with a pharmacy insurance carrier of the patient;

(d) generating, when it is determined if there is a determination that the drug formulary is not in existence, a drug formulary preferred by a pharmacy insurance carrier of the patient by referencing a rules database, the drug formulary matches a formulary identification number of the patient, wherein the formulary identification number is consistent with different insurance carriers of the patient and specific to a formulary;

(e) accessing the information stored in the database for the prescription history, non-prescription purchase history, and prescription purchase history of the patient, wherein access is granted only for the patient or a representative of the patient, under the direction of the patient or the representative, and under the authorization by the patient or the representative;

(f) retrieving the information relating to prescription history, non-prescription purchase history, and prescription purchase history by the patient or the representative; and (g) at least one of printing and displaying, by the patient or the representative, printing the information retrieved relating to the prescription history, non-prescription purchase history, prescription purchase history, and information associated with the formulary, wherein said formulary is associated with the patient's insurance company, to the physician in order to assist the physician in providing medical care to the patient to prescribe for the patient the one or more prescriptions.

48. A computer assisted system for providing, to a physician, information relating to a patient, said method comprising:

(a) means for collecting a prescription history that includes information relating to one or more prescriptions issued to the patient, a non-prescription purchase history comprising at least one of herbal medicines, naturopathic medicines, and over-the-counter medicine, and a prescription purchase history that includes information relating to one or more prescription purchases made by the patient in accordance with the one or more prescriptions and information relating to at least one of past prescriptions issued to the patient by either the treating physician or other physicians, whether or not the prescribed drugs have been purchased by the patient, when the prescribed drugs were purchased, the quantity of prescribed drugs purchased, the number of days past from a refill date when a prescription has not been refilled, when one or more prescriptions are issued by different health care providers, and when or more prescriptions are purchased from different pharmacists including, when information exists, a retail pharmacy, pharmaceutical benefits management company and mail delivery pharmacy;

(b) means for storing the prescription history, non-prescription purchase history, and prescription purchase history information of the patient into a database and storing information relating to pharmacy benefits for the patient and information relating to a drug formulary preferred by a pharmacy insurance carrier of the patient when at least one of the one or more prescriptions are issued by at least one of different health care providers and different pharmacists, wherein the pharmacy includes at least one of a retail pharmacy, pharmaceutical benefits management company, and mail delivery pharmacy;

(c) means for determining whether a drug formulary exists associated with a pharmacy insurance carrier of the patient;

(d) means for generating, when it is determined that the drug formulary is not in existence, a drug formulary associated with the pharmacy insurance carrier of the patient by referencing a rules database, the drug formulary matches a formulary identification number of the patient, wherein the formulary identification number is consistent with different insurance carriers of the patient and specific to a formulary;

(e) means for accessing the prescription history, non-prescription history, and prescription purchase history information of the patient stored in the database, wherein access is granted only for the patient under the direction of the patient and under the authorization by the patient, the database for the stored prescription history, non-prescription purchase history, and prescription purchase history information of the patient;

(f) means for retrieving the prescription history, non-prescription purchase history, and prescription purchase history; and (g) means for at least one of printing and displaying, for the patient, the retrieved prescription history, prescription purchase history, and information associated with the formulary, wherein the formulary is associated with the patient's insurance company to the physician provider in order to assist the provider in providing medical services to the patient, to thereby allow the physician to compare issued one or more prescriptions and the prescription purchase history and prescribe for the patient the one or more prescriptions.

* * * * *